(12) United States Patent
Mezger et al.

(10) Patent No.: US 9,592,320 B2
(45) Date of Patent: *Mar. 14, 2017

(54) CROSSLINKED HUMAN OR ANIMAL TISSUE PRODUCTS AND THEIR METHODS OF MANUFACTURE AND USE

(71) Applicant: Harbor MedTech, Inc., Irvine, CA (US)

(72) Inventors: W. Jerry Mezger, Coto de Caza, CA (US); Keith E. Myers, Lake Forest, CA (US)

(73) Assignee: HARBOR MEDTECH, INC., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/527,571

(22) Filed: Oct. 29, 2014

(65) Prior Publication Data

US 2015/0065429 A1    Mar. 5, 2015

Related U.S. Application Data

(63) Continuation of application No. 13/450,713, filed on Jul. 27, 2012, now Pat. No. 8,901,078.

(60) Provisional application No. 61/512,801, filed on Jul. 28, 2011.

(51) Int. Cl.
| | | |
|---|---|---|
| C09H 1/00 | (2006.01) | |
| A61L 27/24 | (2006.01) | |
| A61K 38/39 | (2006.01) | |
| A61K 38/17 | (2006.01) | |
| A61K 38/16 | (2006.01) | |
| A61L 27/36 | (2006.01) | |
| A61L 27/54 | (2006.01) | |
| A61L 27/58 | (2006.01) | |
| C07K 14/78 | (2006.01) | |

(52) U.S. Cl.
CPC ............. *A61L 27/24* (2013.01); *A61K 38/16* (2013.01); *A61K 38/17* (2013.01); *A61K 38/39* (2013.01); *A61L 27/3687* (2013.01); *A61L 27/54* (2013.01); *A61L 27/58* (2013.01); *C07K 14/78* (2013.01); *A61L 2300/404* (2013.01); *A61L 2430/34* (2013.01); *A61L 2430/40* (2013.01)

(58) Field of Classification Search
None
See application file for complete search history.

(56) References Cited

U.S. PATENT DOCUMENTS

| | | |
|---|---|---|
| 4,806,595 A | 2/1989 | Noishiki et al. |
| 5,080,670 A | 1/1992 | Imamura et al. |
| 5,162,430 A | 11/1992 | Rhee et al. |
| 5,264,214 A | 11/1993 | Rhee et al. |
| 5,292,802 A | 3/1994 | Rhee et al. |
| 5,304,595 A | 4/1994 | Rhee et al. |
| 5,306,500 A | 4/1994 | Rhee et al. |
| 5,308,889 A | 5/1994 | Rhee et al. |
| 5,324,775 A | 6/1994 | Rhee et al. |
| 5,328,955 A | 7/1994 | Rhee et al. |
| 5,376,110 A | 12/1994 | Tu et al. |
| 5,376,375 A | 12/1994 | Rhee et al. |
| 5,413,791 A | 5/1995 | Rhee et al. |
| 5,446,091 A | 8/1995 | Rhee et al. |
| 5,470,911 A | 11/1995 | Rhee et al. |
| 5,475,052 A | 12/1995 | Rhee et al. |
| 5,476,666 A | 12/1995 | Rhee et al. |
| 5,510,121 A | 4/1996 | Rhee et al. |
| 5,510,418 A | 4/1996 | Rhee et al. |
| 5,523,348 A | 6/1996 | Rhee et al. |
| 5,527,856 A | 6/1996 | Rhee et al. |
| 5,543,441 A | 8/1996 | Rhee et al. |

(Continued)

FOREIGN PATENT DOCUMENTS

| | | |
|---|---|---|
| CA | 2247199 | 9/1997 |
| DE | 69722388 | 4/2004 |

(Continued)

OTHER PUBLICATIONS

Crea, J Periodontol, 2008;79:2281-2289.*
Zeeman, 1999, Biomaterials, 20, 921-931.*
Nishi, C., et al., In virtro evaluation of cytotoxicity of diepoxy compounds used for biomaterial modification, Journal of Biomedical Materials Research, vol. 29, pp. 829-823, 1995.
Tattini, Jr. et al., Evaluation of shrinkage temperature of bovine pericardium tissue for bioprosthetic heart valve application by differential scanning calorimetry and freeze-drying microscopy, Materials Research Jul. 12, 2006, pp. 1-4, Vo. 10, No. 1.

(Continued)

*Primary Examiner* — Satyanarayana R Gudibande
(74) *Attorney, Agent, or Firm* — Knobbie, Martens, Olson & Bear, LLP

(57) ABSTRACT

Degradable bioprostheses made of collagen-based material having amine-based and ester-based crosslinks are provided, as are methods for their formation and use. Some embodiments of the present invention are directed towards a method of controlling the ratio of amine-based crosslinks to ester-based crosslinks within a collagen-based material to provide a tailorably crosslinked collagen-based material. Some embodiments provide a method of making a degradable bioprosthesis involving controlling crosslinking to afford a degradable bioprosthesis that is partially crosslinked. By controlling the ratio of amine-based to ester-based crosslinks, by controlling the level of crosslinking, or by controlling both of these features, degradable bioprostheses with tailored degradation rates can be synthesized. Some embodiments of degradable bioprostheses have degradation rates that are tailored to allow their use in particular medical applications. Some embodiments are directed towards methods of use degradable bioprostheses in wound healing, tissue repair, and tissue supplementation.

16 Claims, 5 Drawing Sheets

(56) References Cited

U.S. PATENT DOCUMENTS

| | | | |
|---|---|---|---|
| 5,550,187 A | 8/1996 | Rhee et al. |
| 5,550,188 A | 8/1996 | Rhee et al. |
| 5,565,519 A | 10/1996 | Rhee et al. |
| 5,614,587 A | 3/1997 | Rhee et al. |
| 5,643,464 A | 7/1997 | Rhee et al. |
| 5,744,545 A | 4/1998 | Rhee et al. |
| 5,786,421 A | 7/1998 | Rhee et al. |
| 5,800,541 A | 9/1998 | Rhee et al. |
| 5,827,937 A | 10/1998 | Agerup |
| 5,866,610 A | 2/1999 | Lang et al. |
| 5,880,242 A | 3/1999 | Hu et al. |
| 5,936,035 A | 8/1999 | Rhee et al. |
| 6,117,979 A | 9/2000 | Hendriks et al. |
| 6,156,531 A | 12/2000 | Pathak et al. |
| 6,166,184 A | 12/2000 | Hendriks et al. |
| D461,248 S | 8/2002 | Bianchi et al. |
| 6,482,584 B1 | 11/2002 | Mills et al. |
| 6,497,726 B1 | 12/2002 | Carter et al. |
| 6,613,278 B1 | 9/2003 | Mills et al. |
| 6,652,818 B1 | 11/2003 | Mills et al. |
| 6,690,659 B1 | 2/2004 | Ahmed et al. |
| 6,761,735 B2 | 7/2004 | Eberhardt |
| 6,765,896 B1 | 7/2004 | Ahmed et al. |
| 6,805,713 B1 | 10/2004 | Carter et al. |
| 6,893,462 B2 | 5/2005 | Buskirk et al. |
| 6,914,126 B2 | 7/2005 | Van Dyke |
| 6,947,398 B1 | 9/2005 | Ahmed et al. |
| 6,989,437 B2 | 1/2006 | Van Dyke |
| 7,001,987 B2 | 2/2006 | Van Dyke |
| 7,014,655 B2 | 3/2006 | Barbarash |
| 7,053,051 B2 | 5/2006 | Hendriks et al. |
| 7,479,164 B2 | 1/2009 | Girardot et al. |
| 7,513,910 B2 | 4/2009 | Buskirk et al. |
| 7,579,381 B2 | 8/2009 | Dove |
| 7,704,222 B2 | 4/2010 | Wilk |
| 7,736,327 B2 | 6/2010 | Wilk |
| 7,896,913 B2 | 3/2011 | Damm |
| 7,896,915 B2 | 3/2011 | Guyenot |
| 7,914,575 B2 | 3/2011 | Guyenot |
| 7,918,899 B2 | 4/2011 | Girardot et al. |
| 8,105,379 B2 | 1/2012 | Carter et al. |
| 8,110,001 B2 | 2/2012 | Carter et al. |
| 8,137,411 B2 | 3/2012 | Schankereli |
| 8,142,991 B2 | 3/2012 | Mills et al. |
| 8,153,591 B2 | 4/2012 | Masters et al. |
| 8,167,943 B2 | 5/2012 | Carter et al. |
| 2001/0018614 A1 | 8/2001 | Bianchi |
| 2001/0031254 A1 | 10/2001 | Bianchi et al. |
| 2002/0072806 A1 | 6/2002 | Buskirk et al. |
| 2002/0106393 A1 | 8/2002 | Bianchi et al. |
| 2002/0119437 A1 | 8/2002 | Grooms et al. |
| 2003/0023304 A1 | 1/2003 | Carter et al. |
| 2003/0027125 A1 | 2/2003 | Mills et al. |
| 2003/0097179 A1 | 5/2003 | Carter et al. |
| 2003/0204037 A1 | 10/2003 | Van Dyke |
| 2003/0219486 A1 | 11/2003 | Van Dyke |
| 2003/0224052 A1 | 12/2003 | Van Dyke |
| 2003/0229394 A1 | 12/2003 | Ogle et al. |
| 2004/0059430 A1 | 3/2004 | Kim et al. |
| 2004/0062793 A1 | 4/2004 | Van Dyke |
| 2004/0115172 A1 | 6/2004 | Bianchi et al. |
| 2004/0120910 A1 | 6/2004 | Van Dyke |
| 2004/0210308 A1 | 10/2004 | Carter et al. |
| 2004/0253291 A1 | 12/2004 | Girardot et al. |
| 2005/0096742 A1 | 5/2005 | Mills et al. |
| 2005/0100862 A1 | 5/2005 | Mills et al. |
| 2005/0101957 A1 | 5/2005 | Buskirk et al. |
| 2005/0119744 A1 | 6/2005 | Buskirk et al. |
| 2005/0136510 A1 | 6/2005 | Hendriks et al. |
| 2006/0073207 A1 | 4/2006 | Masters et al. |
| 2006/0159641 A1 | 7/2006 | Girardot et al. |
| 2006/0193885 A1 | 8/2006 | Leonard Neethling et al. |
| 2006/0217804 A1 | 9/2006 | Dove |
| 2006/0217805 A1 | 9/2006 | Dove |
| 2007/0014831 A1 | 1/2007 | Sung et al. |
| 2007/0020225 A1 | 1/2007 | Abramson et al. |
| 2008/0051887 A1 | 2/2008 | Carter et al. |
| 2008/0293637 A1 | 11/2008 | Schroeder et al. |
| 2009/0130162 A2 | 5/2009 | Pathak et al. |
| 2009/0186333 A1 | 7/2009 | Mills et al. |
| 2010/0082104 A1 | 4/2010 | Carter et al. |
| 2010/0099623 A1 | 4/2010 | Schroeder et al. |
| 2010/0099624 A1 | 4/2010 | Schroeder et al. |
| 2010/0143487 A1 | 6/2010 | Masters |
| 2010/0268349 A1 | 10/2010 | Bianchi et al. |
| 2011/0207671 A1 | 8/2011 | Chang et al. |
| 2011/0221096 A1 | 9/2011 | Schankereli |
| 2011/0224779 A1 | 9/2011 | Schankereli |
| 2011/0301707 A1 | 12/2011 | Buskirk et al. |
| 2012/0010146 A1 | 1/2012 | Han et al. |
| 2012/0041539 A1 | 2/2012 | Masters |
| 2012/0165264 A1 | 6/2012 | Malessa et al. |

FOREIGN PATENT DOCUMENTS

| | | | |
|---|---|---|---|
| EP | 0888142 B1 | | 5/2003 |
| EP | 0897942 B1 | | 3/2004 |
| EP | 0898973 B1 | | 1/2005 |
| JP | 2000-506050 | | 5/2000 |
| NL | EP 0898973 | * | 8/1998 |
| WO | WO 94/17841 | | 8/1994 |
| WO | WO 97/32615 | | 9/1997 |
| WO | WO 99/27979 | | 6/1999 |
| WO | WO 02/49687 A1 | | 6/2002 |
| WO | WO 2009/154344 | | 12/2009 |
| WO | WO 2013/016571 A1 | | 1/2013 |

OTHER PUBLICATIONS

Zeeman, Raymond, Cross-linking of collagen-based materials, Thesis, University of Twente, Enschede, The Netherlands, 1998, FEBODRUK BV., The Netherlands.

Zeeman, R., et al., Successive epoxy and carbodiimide cross-linking of dermal sheep collagen, Biomaterial 20 (1999) 921-931.

Search Report and Written Opinion mailed Nov. 7, 2012 in International application No. PCT/US2012/048392.

International Preliminary Report on Patentability and Written Opinion issued Jan. 28, 2014 in corresponding International Patent Application No. PCT/US2012/048392.

Hu, Kuikui, et al., An Experimental Study on Preparing Trestle of Tissue Engineering for Skin by Collagen, Acta Academiae Medicinae Jiangxi, 2005, vol. 45, Issue 6.

* cited by examiner

CROSSLINKED HUMAN OR ANIMAL TISSUE PRODUCTS AND THEIR METHODS OF MANUFACTURE AND USE

CROSS-REFERENCE

This application is a continuation of U.S. patent application Ser. No. 13/560,713, filed Jul. 27, 2012, now U.S. Pat. No. 8,901,078, entitled "Crosslinked Human or Animal Tissue Products and Their Methods of Manufacture and Use," which claims the benefit of U.S. Provisional Application No. 61/512,801, filed Jul. 28, 2011. The contents of all of the above-referenced applications are incorporated by reference herein in their entireties.

BACKGROUND OF THE INVENTION

Field of the Invention

Embodiments of the present invention are directed to controlling a collagen crosslinking process to create crosslinked products with tailorable degradation rates for medical purposes. Further embodiments are directed to products such as skin substitutes and surgical mesh made from such processes, and methods of using such products in medical procedures such as treating chronic wounds, supplementing healing, tissue support, and reconstructive surgery.

Description of the Related Art

Many medical products are composed from human or animal tissue-based materials. Examples of these medical products include, for example, heart valves, vascular grafts, urinary bladder prostheses, tendon prostheses, hernia patches, surgical mesh, and skin substitutes. An illustration of a specific human or animal tissue based product is the heart valve prosthesis. Heart valve prostheses are typically made from either porcine aortic valves or bovine pericardium. Such valves are typically made by pretreating the tissue with glutaraldehyde or other crosslinking agents and sewing the tissue into a flexible metallic alloy or polymeric stent. These animal tissue starting materials mainly consist of collagen, which provides the tissues with their needed mechanical strength and flexibility.

Collagen-based materials, including whole tissue, are finding increased use in the manufacture of biomedical devices, such as prosthetic implants. Collagen is a naturally occurring protein featuring good biocompatibility. It is the major structural component of vertebrates, forming extracellular fibers or networks in practically every tissue of the body, including skin, bone, cartilage, and blood vessels. As a natural component of the extracellular matrix, collagen provides a good physiological, isotropic environment that promotes the growth and function of different cell types and facilitates rapid overgrowth of host tissue in medical devices after implantation.

Basically three types of collagen-based materials can be identified, based on the differences in the purity and integrity of the collagen fiber bundle network initially present in the material. The first type includes whole tissue including non-collagenous substances or cells. As a result of using whole tissue, the naturally occurring composition and the native strength and structure of the collagen fiber bundle network are preserved. Whole tissue xenografts have been used in construction of heart valve prostheses and in many other biomedical prostheses. However, the presence of soluble proteins, glycoproteins, glycosaminoglycans, and cellular components in such whole tissue xenografts may induce an immunological response of the host organism to the implant.

The second type of collagen-based material includes only the collagen matrix without the non-collagenous substances. The naturally occurring structure of the collagen fiber bundle network is thus preserved, but the antigenicity of the material is reduced. The fibrous collagen materials obtained by removing the antigenic non-collagenous substances will generally have suitable mechanical properties.

The third type of collagen-based material is purified fibrous collagen. Purified collagen is obtained from whole tissue by first dispersing or solubilizing the whole tissue by either mechanical or enzymatic action. The collagen dispersion or solution is then reconstituted by either air drying, lyophilizing, or precipitating out the collagen. A variety of geometrical shapes like sheets, tubes, sponges or fibers can be obtained from the collagen in this way. The resulting materials, however, do not have the mechanical strength of the naturally occurring fibrous collagen structure.

A major problem in the use of collagen-based materials for implantation, and especially whole tissue xenografts in which the donor and recipient are phylogenetically distant, is that these materials are prone to acute rejection. This is a rapid and violent immunological reaction that leads to the destruction of the xenograft. In order to use collagen-based materials in manufactured medical devices, particularly bio-prosthetic implants, their durability and in vivo performance typically need to be protected from an acute immunological reaction. This can be done by crosslinking the collagen-based materials to suppress the antigenicity of the material in order to prevent the acute rejection reaction. In addition, crosslinking is used to preserve or even improve mechanical properties and to enhance resistance to degradation.

Crosslinking can be performed by means of physical methods, including, for example, UV irradiation and dehydrothermal crosslinking. These methods result in a direct, but generally low density crosslinking. Several chemical crosslinking methods for collagen-based materials are known. These methods involve the reaction of a bifunctional reagent with the amine groups of lysine or hydroxylysine residues on different polypeptide chains or the activation of carboxyl groups of glutamic and aspartic acid residues followed by the reaction with an amine group of another polypeptide chain to give an amide bond.

Compared with other known methods, glutaraldehyde (GA) crosslinking of collagen provides materials with the highest degree of crosslinking. It is currently the most frequently used chemical crosslinking reagent for collagen-based materials. Glutaraldehyde is a dialdehyde. The aldehyde is able to chemically interact with amino groups on collagen to form chemical bonds. This crosslinking agent is readily available, inexpensive, and forms aqueous solutions that can effectively crosslink tissue in a relatively short period. Using GA crosslinking, increased resistance to biodegradation, reduced antigenicity, and improved mechanical properties of collagen-based materials can be achieved. Despite improved host acceptance, crosslinking of collagen-based materials using GA has shown to have cytotoxic characteristics, both in vitro and in vivo. Also, crosslinking of collagen-based materials using GA tends to result in stiffening of the material and calcification.

Crosslinking can also be accomplished with diisocyanates by bridging of amine groups on two adjacent polypeptide chains. In the first step, reaction of the isocyanate group with a (hydroxy)lysine amine group occurs, resulting in the formation of a urea bond. Thereafter a crosslink is formed by reaction of the second isocyanate group with another amine group. Diisocyanates do not show condensation reactions as observed in GA crosslinking. Also, no residual reagents are left in the material. A disadvantage, however, is the toxicity of diisocyanates and limited water solubility of most diisocyanates.

Another method of crosslinking involves the formation of an acyl azide. The acyl azide method involves the activation of carboxyl groups in the polypeptide chain. The activated groups form crosslinks by reaction with collagen amine groups of another chain. First, the carboxyl groups are esterified by reaction with an alcohol. This ester is then converted to a hydrazide by reaction with hydrazine ($H_2N-NH_2$). Acyl azide groups are formed by reaction with an acidic solution of sodium nitrite. At low temperatures and basic pH values, the acyl azide group reacts with a primary amine group to give amide bonds. This multi-step reaction results in good material properties; however, long reaction times (e.g., 7 days) are necessary. Alternatively, a method has recently been developed that does not need an esterification step or the use of hydrazine. In this method, a carboxyl group is converted to an acyl azide group in one single step by reaction with diphenylphosphorylazide (DPPA). This increases the reaction rate significantly; however, the reaction is carried out in an organic solvent (e.g., DMF), which is undesirable.

Also, water-soluble carbodiimides can be used to activate the free carboxyl groups of glutamic and aspartic acid moieties in collagen. Activation of the carboxyl groups with carbodiimides, such as 1-ethyl-3-(3-dimethyl aminopropyl) carbodiimide.HCl (EDC), gives O-acylisourea groups. A condensation reaction by nucleophilic attack of a free amine group of a (hydroxy)lysine residue with urea as a leaving group results in formation of an amide crosslink. The O-acylisourea can also be hydrolyzed or rearranged to an N-acylurea, which is much more stable and will not react to form a crosslink. Addition of N-hydroxysuccinimide (NHS) prevents this rearrangement, however. In the presence of NHS, the O-acylisourea can be converted to an NHS activated carboxyl group, which also can react with a free amine group to form a crosslink. Addition of NHS increases the reaction rate. Also, crosslinking with EDC and NHS provides collagen material with a high degree of crosslinking; however, it also results in a material with a low tensile strength.

Yet another crosslinking method uses epoxy compounds to crosslink collagen. See, for example, U.S. Pat. No. 4,806,595 (Noishiki et al.), U.S. Pat. No. 5,080,670 (Imamura et al.), U.S. Pat. No. 5,880,242 (Hu, et al.), U.S. Pat. No. 6,117,979 (Hendriks et al.), and U.S. Pat. No. 7,918,899 (Girardot et al.). Epoxy compounds (i.e., epoxides) can undergo both acid-catalyzed and base-catalyzed reactions with a number of functional groups, including amine groups and carboxylic acid groups, under the appropriate conditions. Typically, the crosslinking of collagen with epoxides is carried out at basic pH (e.g., pH 8-10) with the result that crosslinking occurs through the free amine groups of the collagen.

Common to all of these crosslinking methods is the objective to "fully crosslink" the collagen (generally regarded as achieving crosslinks among at least 80% of the collagen molecules) in order to create products with low immunogenicity and a high resistance to enzymatic attack by the host body (and therefore very long term durability). However, there remains a need to create products, specifically collagen-based materials, that have great durability (defined as retaining high strength following implant) but which are intended to degrade during healing such that they are essentially fully dissolved when the healing process is complete.

Despite the wide variety of crosslinking agents available, the degradation profiles of prosthetic collagen materials currently in use for general surgical reconstruction fall into only two categories: 1) those prosthetic collagen materials that quickly bioresorb when in use, or 2) those prosthetic collagen materials that last longer than one year in use and, for all intents and purposes, are non-bioresorbable. Within the category of quickly bioresorbed materials, two classes of bioprosthetic collagen materials dominate. The first of such materials are collagen-based materials that have not been cross-linked (e.g. native collagen). The second is collagen that is fully crosslinked but with crosslinks that are hydrolyzable, such as ester-based crosslinks. Generally, quickly bioresorbable collagen materials have a functional duration of 6 to 8 weeks in normal in vivo conditions (such as in a wound or surgical site). The time taken to bioresorb may be even less in more proteolytic environments such as in chronic wounds such as diabetic foot ulcers. During biodegradation, these quickly bioresorbable collagenous materials often prematurely lose strength and other important functional characteristics before the wound is completely healed, thereby compromising the long term success of the medical procedure.

Non-bioresorbable extracellular collagen matrices are historically fully cross-linked materials with non-hydrolyzable crosslinks. Typical examples include collagen that has amine-based crosslinks. The amine-based crosslinking provides a material that is non-bioresorbable in the in vivo biologic environment. Fully crosslinked extracellular collagen materials with non-hydrolyzable crosslinks currently tend to last many years, if not a lifetime, when used for surgical repair or reconstruction. While such materials retain strength during the healing process, their long presence can be problematic.

SUMMARY OF THE INVENTION

Given the limitations of current collagen-based biomaterials, certain embodiments of the present application provide methods synthesizing degradable bioprostheses (or singularly a degradable bioprosthesis), compositions of degradable bioprostheses, products made therefrom, and methods of using said products and compositions. Some embodiments provide a method of making a degradable bioprosthesis. In one embodiment, a method comprises providing a collagen-based material, exposing the collagen-based material to a first buffered solution with a pH between 8.0 to 10.5 (or between about 8.0 to about 10.5) for a first period of time to provide a treated collagen-based material, wherein the first buffered solution comprises a concentration of a first crosslinking agent, exposing the treated collagen-based material to a second buffered solution with a pH between 3.0 to 5.5 (or between about 3.0 to about 5.5) for a second period of time to provide a tailorably crosslinked collagen-based material, wherein the second buffered solution comprises a concentration of a second crosslinking agent, and isolating the tailorably crosslinked collagen-based material to provide a degradable bioprosthesis. In some embodiments, a bioprosthesis made by the method above is provided.

Another embodiment of a method of making a degradable bioprosthesis comprises providing a collagen-based material and controllably crosslinking the collagen so that only a portion of the collagen is crosslinked. In some embodiments a bioprosthesis made by the method above is provided. Other methods of making a biodegradable bioprosthesis are described below.

In some embodiments, a crosslinked collagen-based material is provided. In one embodiment, a crosslinked collagen-based material comprising Crosslink A and Crosslink B represented by

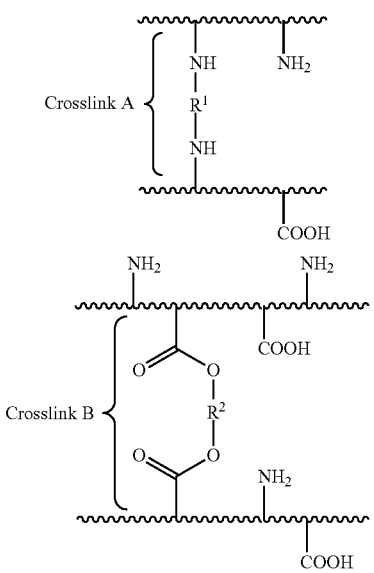

wherein ᴠᴠᴠ indicates collagen strands, $R^1$ is

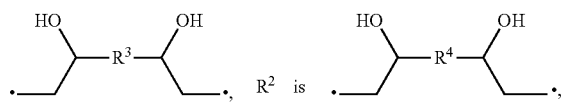

and $R^3$ and $R^4$ are independently selected from the group consisting of —$(CH_2)_n$— and —$O(CH_2)_n)_m$—, where n and m are independently an integer from 1-6, and the amount of free amines (—$NH_2$) on the collagen strands is between 50% and 85% (or between about 50% and about 85%) is provided. Other methods of making a biodegradable bioprosthesis are described below.

Some embodiments provide a degradable bioprosthesis comprising a crosslinked collagen-based material comprising Crosslink A and Crosslink B:

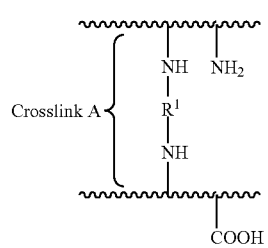

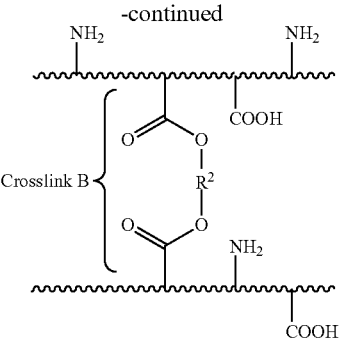

wherein ᴠᴠᴠ indicates collagen strands, $R^1$ is

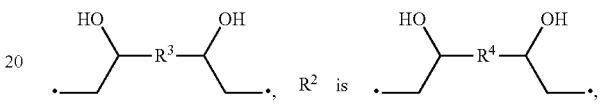

and $R^3$ and $R^4$ are independently selected from the group consisting of —$(CH_2)_n$— and —$(O(CH_2)_n)_m$—, where n and m are independently an integer from 1-6, and the amount of free amines (—$NH_2$) on the collagen strands is between 50% and 85% (or between about 50% and about 85%) is provided.

Some embodiments provide a degradable bioprosthesis comprising a tailorably crosslinked collagen-based material. In one embodiment, a collagen-based material comprises collagen strands that further comprise amine-based crosslinks and ester-based crosslinks, and the tailorably crosslinked collagen-based material has a degradation rate between 0.2% to 1.0% (or between about 0.2% to about 1.0%) per hour when subjected to a pronase digestion assay. Other embodiments of a degradable bioprosthesis are described below.

In another embodiment, a degradable bioprosthesis comprising a biologic skin substitute comprising collagen that is between 20% to 80% (or between about 20% to about 80%) crosslinked is provided.

Some embodiments provide a method of treating a tissue defect. In one embodiment, the method comprises positioning a degradable bioprosthesis such as described above or further herein at, over, or into the tissue defect, wherein the degradable bioprosthesis comprises a crosslinked collagen-based material having a degradation rate between about 0.2% to about 1.0% per hour when subjected to a pronase digestion assay.

Some embodiments provide a method of treating a wound. In one embodiment, the method comprises identifying a patient in need of a degradable bioprosthesis to aid in the healing of a wound, determining an approximate rate of healing of the wound, selecting a degradable bioprosthesis comprising a tailorably crosslinked collagen-based material having a degradation rate similar to the rate of healing of the wound, and implanting the degradable bioprosthesis over or into the wound.

In another embodiment, a method of treating a wound comprises providing a biologic skin substitute comprising partially crosslinked collagen and placing the skin substitute over a wound, wherein the degradation of the skin substitute progresses at or about the same rate as the wound heals. Other embodiments of methods of treatment are described below. Such methods may utilize any of the compositions, materials, bioprostheses or other structures described herein.

DETAILED DESCRIPTION OF CERTAIN EMBODIMENTS OF THE INVENTION

Figure 1:
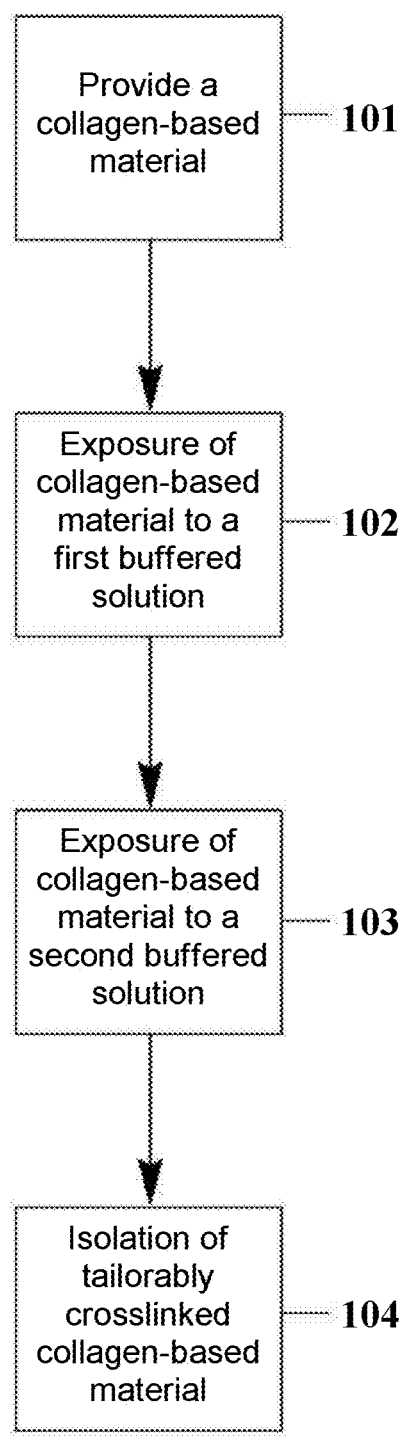
FIG. 1 is a flow chart depicting an embodiment of the method of synthesizing a tailorably crosslinked collagen-based bioprosthesis.

This disclosure is related to compositions and methods of synthesizing and using tailored crosslinked collagen-based animal or human tissue to afford bioprosthetic devices with tailored degradation rates.

As used herein, the term "collagen-based material" refers to materials that have been excised from animal or human tissue, which may or may not be crosslinked. Depending on the level of processing of natural tissue, collagen-based materials may include collagen, tropocollagen, collagen fibrils, or collagen fibers. Collagen exists as a triple helix of amino acid chains. These triple helical chains, called tropocollagen, further assemble to form collagen fibrils. These collagen fibrils assemble to form collagen fibers.

As used herein, the term "collagen strand" refers to tropocollagen, collagen fibrils and/or collagen fibers. Collagen strands have pendant amine (—$NH_2$) and carboxylic acid (—COOH) groups which are reactive. These amines and carboxylic acid groups are readily crosslinked between collagen strands with various crosslinking agents to form structures with improved medial properties. Crosslinking can be performed by taking advantage of pendant reactive groups on the collagen strand.

As used herein, the term "degradation time" refers to the amount of time it takes for a collagen-based material to completely degrade or to degrade to such an extent that it no longer serves the purpose for which it was medically intended.

As used herein, the term "diepoxide" refers to a compound that has two reactive epoxide functionalities. Epoxides have long been used as crosslinking agents for collagen because, when fully reacted, epoxide crosslinking reduces the immunogenicity of collagen while improving the physical properties of the material. Useful diepoxides may include, but are not limited to, glycol diglycidyl ether, glycerol diglycidyl ether, butanediol diglycidyl ether, resorcinol diglycidyl ether, 1,6-hexanediol diglycidyl ether, ethylene glycol diglycidyl ether, diethylene glycol diglycidyl ether, triethylene glycol diglycidyl ether, polyethylene glycol diglycidyl ether, propylene glycol diglycidyl ether, dipropylene glycol diglycidyl ether, and polybutadiene, diglycidyl ether. An example of the diepoxide that can be used to crosslink collagen strands is 1,4 butanediol diglycidyl ether (BDDGE).

As used herein, the term "crosslinking agent" may refer to diepoxides or compounds with three or more pendant epoxide functional groups. Useful crosslinking agents may include, but are not limited to, the above mentioned diepoxides, glycerol triglycidyl ether, sorbitol polyglycidyl ether, polyglycerol polyglycidyl ether, pentaerythritol polyglycidyl ether, diglyceryl polyglycidyl ether, glycerol polyglycidyl ether, and trimethylolpropane polyglycidyl ether.

An unmet need in the area of wound healing, general surgery, and orthopedic surgery is for a collagen-based material that can be tailored to degrade at intervals, for example, greater the 8 weeks but of less than 1 year. This tailored degradation rate can be made to comport with the healing cycle of each specific condition. Examples of these conditions include procedures such as hernia repair, diabetic foot ulcer healing and orthopedic tendon repairs to name only a few. Embodiments of the current invention are targeted towards compositions that have tailorable degradation times.

Some embodiments of the present invention are directed towards controlling the ratio of amine-based crosslinks to ester-based crosslinks within a collagen-based material to provide a tailorably crosslinked collagen-based material. The inventors of the present invention have surprisingly found that by controlling the pH and reaction time during the crosslinking of collagen-based materials using epoxides, a tailorably crosslinked collagen-based material can be obtained. While not bound by any particular theory, the inventors have found that by controlling the pH of the reaction, the ratio of amine-based crosslinking (Crosslink A) to ester-based crosslinking (Crosslink B) in a collagen-based material can be controlled to afford a bioprosthesis with a controllably tailored degradation rate. As mentioned previously, the amine-based crosslinks form stable bonds. Thus, the higher the ratio of amine-based crosslinks, the lower the degradation rate of the collagen-based materials. Alternatively, the ester-based crosslinks hydrolyze quickly in vivo. Thus, the higher the ratio of ester-based crosslinks, the higher the degradation rate of the collagen-based materials. By manipulating the ratio of amine and ester-based crosslinks, the degradation rate can be tailorably adjusted to clinically relevant timeframes.

In some embodiments, the diepoxide BDDGE has been shown to fully crosslink collagen at a concentration of 4% weight to volume, a pH of below 6, and a reaction time of 160 hours. As used herein, the term "% weight to volume" or "% w/v" refers to the weight of solute (g)/volume of solution (mL)×100. It is believed that at low pH (e.g., 3.0-5.5 pH), crosslinking primarily occurs through a reaction of carboxylates on the collagen strand with epoxides on the BDDGE. At low pH, it is believed that carboxylic acids of the collagen strand are more nucleophilic than amine groups of the collagen strand. At low pH, some amount of carboxylic acid group exists as a carboxylate (—$RCOO^{\ominus}$) which is to some degree nucleophilic, while the amine group is primarily protonated to form a primary ammonium (—$R'NH_3^{\oplus}$), which is not nucleophilic. The carboxylate, therefore, preferentially acts as a nucleophile in a reaction with an epoxide crosslinking agent. The resulting functional group is an ester, thus forming an ester-based crosslink (as shown below).

∼∼∼ indicates a collagen strand

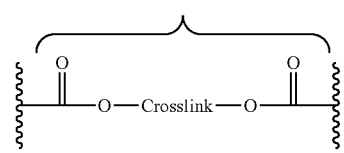

Ester-based crosslinks, are readily hydrolyzable and are quickly bioresorbable. Thus, the degradation time of collagen that is fully crosslinked with ester-based crosslinks is near that of native collagen at around 8 weeks or less. Thus, despite improved immunogenicity over native collagen, crosslinking through these ester groups does little to slow the degradation rate of native collagen. The degradation rate of collagen is measured by a % loss in mass over unit of time measured in hours. One of skill in the art will also recognize that when diepoxide-based crosslinking is carried out at low pH, some amount of amine-based crosslinks will likely form, as well as crosslinks that are based on the reaction of both a carboxylate and an amine with a diepoxide (a hetero-crosslink).

It is also known that crosslinking collagen at 9.2 pH with BDDGE for 160 hours will fully crosslink the collagen. While not bound by any particular mechanism, it is believed that this crosslinking occurs primarily through the amine groups on the collagen strands, which at higher pH exist to some degree as highly nucleophilic free amines ($-R'NH_2$). The resulting functional group from the reaction of an amine with an epoxide is an amine, thus this is an amine-based crosslink.

∼∼∼ indicates a collagen strand

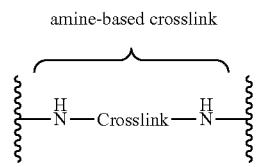

amine-based crosslink

These amine-based crosslinking lead to a non-bioresorbable material with a degradation rate that exceeds a year in vivo. Because the amine-based crosslink is so strong, it does not degrade easily under typical in vivo conditions. One of skill in the art will also recognize that when diepoxide-based crosslinking is carried out at a high pH, some amount of ester-based crosslinks will likely form, as well as crosslinks that are based on the reaction of both a carboxylate and an amine with a diepoxide (a hetero-crosslink).

In some embodiments, the reaction time is long enough to ensure substantially complete crosslinking of the collagen strands. The substantially complete crosslinking of these collagen strands may be important for 1) instilling the crosslinked collagen-based material with good mechanical properties and 2) reducing the number of pendant unreacted epoxide functional groups bound to the crosslinked collagen-based material and therefore lowering cytotoxicity. In some embodiments, reaction times are sufficient to decrease the number of pendant epoxides to such a degree that the resulting materials are biocompatible. Thus, embodiments of the current strategy results in a crosslinked material which is highly tailorable and biocompatible.

In some embodiments, the ratio of Crosslink A to Crosslink B can be adjusted by controlling the amount of time a collagen-based material is exposed to a buffered solution of a diepoxide at a first pH, then by controlling the amount of time the treated material is exposed to a second buffered solution of a diepoxide at a second pH.

Embodiments of the present invention provide methods of making a degradable bioprosthesis (for example, an implant or implantable device, or a topically applied wound dressing) comprising collagen-based material that has been controllably crosslinked and is intentionally designed to degrade over a proscribed period of time in the body, with such time generally less than one year. In some embodiments, these methods also involve partially crosslinking the collagen-based material. Advantageously, these methods yield a material with a predictably, and repeatedly moderate degree of crosslinking, variable crosslink stabilities, and a moderate/tailored resistance towards enzymatic digestion following implantation.

Method of Making Bioprosthesis

Some embodiments provide a method of making a degradable bioprosthesis as shown in FIG. 1. First step 101 involves providing a collagen-based material. In some embodiments, animal or human tissue is dissected and undergoes a decellularization process to result in the collagen-based material. In some embodiments, depending on the level of processing of natural tissue, collagen-based materials may be collagen, tropocollagen, collagen fibrils, or collagen fibers. In some embodiments the collagen-based material is excised from the pericardium of an animal or a human.

Step 102 involves exposing the collagen-based material to a first buffered solution comprising a first crosslinking agent at a first pH for a first period of time to provide a treated collagen-based material. In some embodiments, the first pH is high enough to result in crosslinks that are primarily amine-based. In some embodiments, the first buffered solution has a pH between 8.0 to 10.5 (or about 8.0 to about 10.5). In some embodiments, the pH of the first buffered solution may be from 8.9 to 9.5 (or about 8.9 to about 9.5), from 9.0 to 9.4 (or about 9.0 to about 9.4), or from 9.1 to 9.3 (or about 9.1 to about 9.3). In some embodiments, the pH of the first buffered solution may be 9.2 (or about 9.2). The concentration of first crosslinking agent in the first solution may be from 1% to 10% (or from about 1% to about 10%) (w/v), from 2% to 8% (or from about 2% to about 8%) (w/v), from 3% to 7% (or about 3% to about 7%) (w/v), or from 4% to 6% (or about 4% to about 6%) (w/v). In some embodiments, the first crosslinking agent concentration in the first solution is 4% (or about 4%) (w/v). The first period of time for the crosslinking reaction depends on the desired level of crosslinking, and may be from 0.5 hours to 64 hours (or about 0.5 hours to about 64 hours). In some embodiments, the first period of time may be from 1 hour to 60 hours (or about 1 hour to about 60 hours), from 10 hours to 50 hours (or about 10 hours to about 50 hours), or from 20 hours to 40 hours (or about 20 hours to about 40 hours). In some embodiments the first period of time may be from 0.5 hours to 10 hours (or about 0.5 hours to about 10 hours), from 10 hours to 20 hours (or about 10 hours to about 20 hours), from 20 hours to 30 hours (or about 20 hours to about 30 hours), from 30 hours to 40 hours (or about 30 hours to about 40 hours), from 40 hours to 50 hours (or about 40 hours to about 50 hours), from 50 hours to 60 hours (or about 50 hours to about 60 hours), or from 60 hours to 64 hours (or about 60 hours to about 64 hours). In some embodiments, the treated collagen-based material comprises partially crosslinked collagen strands, and the crosslinks are primarily amine-based crosslinks.

Step 103 involves exposing the treated collagen-based material to a second buffered solution comprising a second crosslinking agent at a low pH for a second period of time to provide a tailorably crosslinked collagen-based material. The pH of the second buffered solution is low enough to result in crosslinks that are primarily ester-based. In some embodiments, the pH of the second buffered solution may be from 3.0 to 5.5 (or about 3.0 to about 5.5). In some embodiments, the pH of the second buffered solution may be from 4.2 to 4.8 (or about 4.2 to about 4.8), from 4.3 to 4.7 (or about 4.3 to about 4.7), or from 4.4 to 4.6 (or about 4.4 to about 4.6). In some embodiments, the pH of the second buffered solution may be 4.5 (or about 4.5). The concentration of second crosslinking agent in the second solution may be from 1% to 10% (or from about 1% to about 10%) (w/v), from 2% to 8% (or from about 2% to about 8%) (w/v), from 3% to 7% (or about 3% to about 7%) (w/v), or from 4% to 6% (or about 4% to about 6%) (w/v). In some embodiments, the first crosslinking agent concentration in the first solution is 4% (or about 4%) (w/v). The second period of time for the crosslinking may be from 100 hours to 160 hours (or about 100 hours to about 160 hours). In some embodiments, the second period of time for the crosslinking may be from 100 hours to 170 hours (or about 100 hours to about 170 hours), from 110 hours to 160 hours (or about 110 hours to about 160 hours), from 120 hours to 150 hours (or about 120 hours to about 150 hours), or from 130 hours to 140 hours (or about 130 hours to about 140 hours). In some embodiments, the second period of time for the crosslinking may be from 100 hours to 110 hours (or about 100 hours to about 110 hours), from 110 hours to 120 hours (or about 110 hours to about 120 hours), from 120 hours to 130 hours (or about 120 hours to about 130 hours), from 130 hours to 140 hours (or about 130 hours to about 140 hours), from 140 hours to 150 hours (or about 140 hours to about 150 hours), from 150 hours to 160 hours (or about 150 hours to about 160 hours), or from 160 to 170 hours (or about 160 hours to about 170 hours). In some embodiments, the second period of time for the crosslinking may be performed for a period that exceeds 170 hours.

In some embodiments, the second period of time for the crosslinking is enough to reduce the amount of pendant epoxides to the point that the material is no longer cytotoxic.

In some embodiments, the total exposure time to the first and second buffered solutions (the total of the first period of time and the second period of time) is such that the resulting tailorably crosslinked collagen-based material is substantially fully crosslinked. In some embodiments, the total exposure time will be sufficient to afford a material that contains a small enough amount of pendant free epoxides such that the material is biocompatible. In some embodiments, the sum of the first period of time and the second period of time is from 100.5 hours to 110 hours (or about 100.5 hours to about 110 hours), from 110 hours to 120 hours (or about 110 hours to about 120 hours), from 120 hours to 130 hours (or about 120 hours to about 130 hours), from 130 hours to 140 hours (or about 130 hours to about 140 hours), from 140 hours to 150 hours (or about 140 hours to about 150 hours), and/or from 150 hours to 160 hours (or about 150 hours to about 160 hours). In some embodiments, the sum of the first period of time and the second period of time is 160 hours (or about 160 hours). In some embodiments, the sum of the first and second periods of time is longer than 160 hours.

Alternatively, the pH of the buffered solutions and reaction times in steps 102 and 103 may be reversed in some embodiments. In some embodiments, step 102 is performed before step 103. In other embodiments, the step 102 may follow step 103. The collagen-base material may be exposed to a crosslinking agent solution with a low pH first, and then a second crosslinking agent solution with a high pH second. In this case, the first buffered solution has a low pH, while the second buffered solution has a high pH.

The crosslinking agents in steps 102 and 103 (the first crosslinking agent and the second crosslinking agent) may be an epoxide. In some embodiments, the first crosslinking agent and the second crosslinking agent may be diepoxide. In some embodiments, the first and second crosslinking agents are independently selected from the group consisting of glycol diglycidyl ether, glycerol diglycidyl ether, glycerol triglycidyl ether, and butanediol diglycidyl ether. In some embodiments, the first and the second crosslinking agents are the same. In some embodiments, the first and second crosslinking agents are BDDGE. In some embodiments, the first and second crosslinking agents used in the present invention are water soluble, non-polymeric epoxies such as polyol polyglycidylethers.

Step 104 involves isolating the tailorably crosslinked collagen-based material to provide a degradable bioprosthesis. The tailorably crosslinked collagen-based material comprises Crosslink A and Crosslink B. In some embodiments, the ratio of Crosslink A to Crosslink B is from 90:10 to 10:90 (or about 90:10 to about 10:90), from 80:20 to 20:80 (or about 80:20 to about 20:80), from 70:30 to 30:70 (or from about 70:30 to about 30:70), from 60:40 to 40:60 (or about 60:40 to about 40:60), or 1:1 (or about 1:1). In some embodiments, the concentration of the first crosslinking agent in the first solution may be from may be from 1% to 10% (or from about 1% to about 10%) (w/v), from 2% to 8% (or from about 2% to about 8%) (w/v), from 3% to 7% (or about 3% to about 7%) (w/v), or from 4% to 6% (or about 4% to about 6%) (w/v), or 4% (or about 4%). In some embodiments, the concentration of the second crosslinking agent in the second solution may be from 1% to 10% (or from about 1% to about 10%) (w/v), from 2% to 8% (or from about 2% to about 8%) (w/v), from 3% to 7% (or about 3% to about 7%) (w/v), or from 4% to 6% (or about 4% to about 6%) (w/v), or 4% (or about 4%).

In some embodiments, the amount of free amines on the crosslinked collagen-based material ranges from 50% to 85% (or about 50% to about 85%), 60% to 75% (or about 60% to about 75%), from 65% to 70% (or about 65% to about 70%), or from 65% to 70% (or about 65% to about 70%), relative to the number of free amines on the collagen-based material before exposing to any crosslinking agent.

Some embodiments provide a method of making a degradable bioprosthesis involving controlling the crosslinking to afford a degradable bioprosthesis that is partially crosslinked. In some embodiments, to create a partially crosslinked degradable bioprosthesis, the crosslinking reaction can be slowed down. In some embodiments, for example, the crosslinking reaction can be slowed by decreasing the concentration of the crosslinking agent, such as from 10% down to 1% in solution (or about 10% to about 1%). In some embodiments, the concentration of crosslinking agent can be controlled within the range from 1% to 2% (or about 1% to about 2%), from 2% to 3% (or about 2% to about 3%), from 3% to 4% (or about 3% to about 4%), from 4% to 5% (or about 4% to about 5%), from 5% to 6% (or about 5% to about 6%), from 6% to 7% (or about 6% to about 7%), from 7% to 8% (or about 7% to about 8%), from 8% to 9% (or about 8% to about 9%), or from 9% to 10% (or about 9% to about 10%).

In some embodiments, the method comprises combining a crosslinking agent with the collagen-based material in an aqueous medium at a basic or an acidic pH to react with a predetermined portion of the collagen amine or carboxyl groups to form a degradable bioprosthesis.

In some embodiments, the crosslinking reaction can be slowed down by reducing the acidity of a crosslinking reaction agent intended to react with the collagen carboxyl groups, or reducing the alkalinity of a crosslinking reaction agent intended to react with the collagen amine groups. In some embodiments, the crosslinking reaction can be slowed down, for example, by reducing the temperature at which the crosslinking reaction takes place. In some embodiments, the crosslinking reaction can be slowed down, for example, by reducing the pressure at which the crosslinking reaction takes place.

In some embodiments, to create a partially crosslinked degradable bioprosthesis, the length of time the collagen-based material is exposed to the crosslinking reaction agent is reduced. In some embodiments, to create a partially crosslinked degradable bioprosthesis, the collagen-based material is masked by chemical or physical means, allowing exposure of only part of the collagen-based material to the crosslinking reaction agent. In some embodiments, another way to create a partially crosslinked degradable bioprosthesis is to expose only a portion, or less than all surfaces, of the collagen-based material to the crosslinking reaction agent.

All of these aforementioned methods to slow the crosslinking reaction or to shorten the reaction time, or to slow, inhibit, limit or prevent exposure of the collagen-based material to the crosslinking reaction agent can be used individually, or in any combination to achieve the optimum material properties.

For example, in some embodiments, reducing the concentration of the crosslinking agent from 5% to 1% in combination with reducing the pH of the crosslinking agent from 10 to 8.5, will substantially slow the crosslinking reaction. In some embodiments, exposing only one surface or side of the collagen-based material to the crosslinking reaction agent can slow or inhibit the crosslinking reaction and thereby limit the amount of collagen that is crosslinked.

Further details regarding cross-linking processes and materials relevant to this disclosure are described in U.S. Pat. No. 5,880,242, the entirety of which is hereby incorporated by reference.

Embodiments of the present invention achieve a predetermined degree of crosslinking by precise control of the concentration of the crosslinking agent, the pH of the crosslinking agent, the length of time the collagen-based material is exposed to the crosslinking agent, and the temperature at which the collagen-based material is exposed to the crosslinking agent. One preferred degree of crosslinking would be crosslinking only about 50% of the free amine or carboxyl groups which would enable the degradable bioprosthesis to retain sufficient resistance to premature enzymatic degradation and retain sufficient strength to complete its intended therapeutic role, yet allow the bioprosthetic device to ultimately dissolve, thereby avoiding a permanent implant.

One method of forming, for example, a partially crosslinked skin substitute begins with a collagen-based material such as porcine pericardium that is first cleaned of foreign material. Then the collagen-based material is treated with a generic detergent solution to remove the animal cellular material, leaving behind principally the extracellular matrix consisting almost entirely of type 1 collagen. The extracellular matrix is then mounted on a frame and soaked for about 50 to about 150 hours in the crosslinking reaction agent, such as BDDGE, that has been diluted to the desired concentration (ranging from about 1% to about 10%). During the crosslinking process, the temperature of the crosslinking reaction agent is maintained at a set temperature (ranging from about −50° C. to about 100° C.), or at different temperatures at pre-programmed intervals. At the completion of the crosslinking reaction, the extracellular matrix is removed from the crosslinking reaction agent, thoroughly rinsed with water to remove the crosslinking agent, then dried, packaged, sterilized.

Crosslinked Collagen-Based Material

Some embodiments provide a crosslinked collagen-based material comprising Crosslink A and Crosslink B:

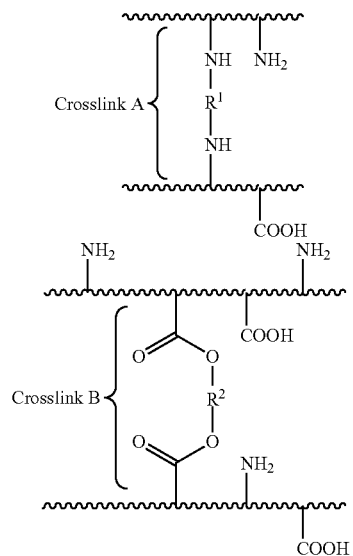

where ∼∼∼ indicates collagen strands; $R^1$ from Crosslink A is further defined as

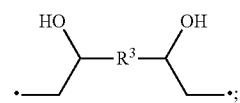

and $R^2$ from Crosslink B is further defined as

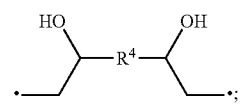

$R^3$ and $R^4$ are independently selected from the group consisting of —$(CH_2)_n$— and —$(O(CH_2)_n)_m$—, where n and m are independently an integer from 0-6; and the amount of free amines (—$NH_2$) on the collagen strands is between 50% and 85% (or between about 50% and about 85%), relative to the number of free amines on the collagen-based material before any reaction.

In some embodiments, $R^3$ and $R^4$ are the same. In some embodiments, the $R^1$ and $R^2$ from above are the same. In some embodiments, the amount of free amines on the crosslinked collagen-based material ranges from 60% to 75% (or about 60% to about 75%), or from 65% to 70% (or about 65% to about 70%), relative to the number of free amines on the collagen-based material before exposing to any crosslinking agent. In some embodiments, the crosslinked collagen-based material further comprises free carboxylic acid groups. In some embodiments, the un-reacted collagen-based material has a first percentage of free amine groups on its collagen strands and the crosslinked collagen-based material has a second percentage of free amine groups, wherein the second percentage of free amine groups is lower than the first percentage as described below. In some embodiments, the crosslinked collagen-based material has a percentage of amines that is lower than that of native collagen.

In some embodiments, the free amine groups of the tailorably crosslinked collagen-based material may be blocked using a blocking agent. A blocking agent is a mono-functional reactive moiety capable of forming a stable covalent bond with a free amine or carboxyl groups in the proteins, thereby blocking crosslinking. Typical blocking agents include compounds containing one amine group or one carboxylic acid group, to block free carboxylic acids and free amines respectively.

In some embodiments, the ratio of Crosslink A to Crosslink B on the crosslinked collagen-based material ranges from 100:1 to 1:100 (or about 100:1 to about 1:100). In some embodiments, the ratio of Crosslink A to Crosslink B is from 90:10 to 10:90 (or about 90:10 to about 10:90), 80:20 to 20:80 (or about 80:20 to about 20:80), from 70:30 to 30:70 (or about 70:30 to about 30:70), from 60:40 to 40:60 (or about 60:40 to about 40:60), or 1:1 (or about 1:1).

Bioprosthesis

Some embodiments provide a degradable bioprosthesis synthesized using any of the methods described above. In some embodiments, the degradable bioprosthesis comprises a crosslinked collagen-based material comprising Crosslink A and Crosslink B:

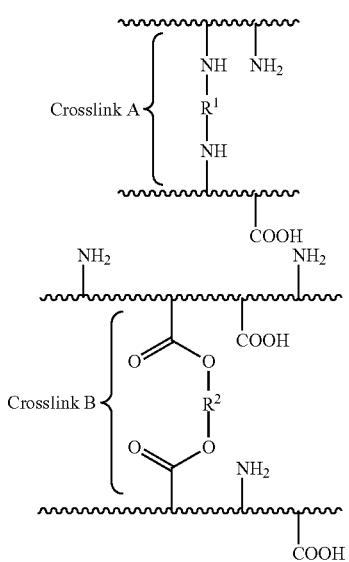

where ⁓ indicates collagen strands; R¹ from Crosslink A is further defined as

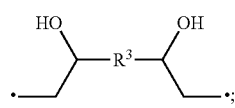

and R² from Crosslink B is further defined as

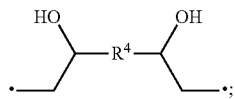

R³ and R⁴ are independently selected from the group consisting of —(CH$_2$)$_n$— and —(O(CH$_2$)$_n$)$_m$—, where n and m are independently an integer from 0-6; and the amount of free amines (—NH$_2$) on the collagen strands is between 50% and 85% (or between about 50% and about 85%), relative to the number of free amines on the collagen-based material before any reaction.

In some embodiments, R³ and R⁴ are the same. In some embodiments, the R¹ and R² from above are the same. In some embodiments, the amount of free amines on the degradable bioprosthesis ranges from 60% to 75% (or about 60% to about 75%), or from 65% to 70% (or about 65% to about 70%), relative to the number of free amines on the collagen-based material before exposing to any crosslinking agent.

In some embodiments, the ratio of Crosslink A to Crosslink B on the degradable bioprosthesis ranges from 100:1 to 1:100 (or about 100:1 to about 1:100). In some embodiments, the ratio of Crosslink A to Crosslink B is from 90:10 to 10:90 (or about 90:10 to about 10:90), 80:20 to 20:80 (or about 80:20 to about 20:80), from 70:30 to 30:70 (or about 70:30 to about 30:70), from 60:40 to 40:60 (or about 60:40 to about 40:60), or 1:1 (or about 1:1).

In some embodiments, the degradable bioprosthesis comprises a tailorably crosslinked collagen-based material as described above, wherein the tailorably crosslinked collagen-based material comprises amine-based crosslinks and ester-based crosslinks in the ratios described above. In some embodiments, as described above, the degradable bioprosthesis further comprises free amines.

In some embodiments, the degradable bioprosthesis has a degradation rate of between about 0.2% to about 1.0% per hour when measured using the pronase digestion assay described in the EXAMPLES section. In some embodiments, the degradable bioprosthesis has a degradation rate that ranges from 0.1% to 1.10% (or about 0.1% to about 1.10%) per hour, from 0.3% to 1.0% (or about 0.3% to about 1.0%) per hour, from 0.4% to 0.9% (or about 0.4% to about 0.9%) per hour, from 0.5% to 0.8% (or about 0.5% to about 0.8%) per hour, from 0.6% to 0.7% (or about 0.6% to about 0.7%) per hour, from 0.2% to 0.3% (or about 0.2% to about 0.3%) per hour, from 0.3% to 0.4% (or about 0.3% to about 0.4%) per hour, from 0.4% to 0.5% (or about 0.4% to about 0.5%) per hour, from 0.5% to 0.6% (or about 0.5% to about 0.6%) per hour, from 0.6% to 0.7% (or about 0.6% to about 0.7% per hour), from 0.7% to 0.8% (or about 0.7% to about 0.8%) per hour, from 0.8% to 0.9% (or about 0.8% to about 0.9%) per hour, from 0.9% to 1.0% (or about 0.9% to about 1.0% per hour), or from 1.0% to 1.1% (or about 1.0% to about 1.1% per hour). It will be appreciated by one of ordinary skill in the art that pronase degradation, enzyme-based degradation, and protease-based degradation test results will have variable degradation rates depending on the type of test used and/or the conditions used during testing.

Heating collagen will induce a structural transition of the native triple helical structure at a certain temperature dependent on the nature and degree of crosslinking. Introduction of covalent crosslinks will increase the stability of the triple helix, thus increasing the denaturation temperature. The temperature at which denaturation takes place is also often referred to as shrinkage temperature (Ts), as shrinkage is the macroscopic manifestation of the transformation of the native triple helix structure to the random coil configuration. Thus, Ts can be used to measure the level of crosslinking. In some embodiments, the Ts of the degradable bioprosthesis is higher than that of native collagen. In some embodiments, the Ts of the degradable bioprosthesis is above 70° C. (or about 70° C.). In some embodiments, the degradable bioprosthesis has a Ts of above 75° C. (or about 75° C.), above 77° C. (or about 77° C.), or above 78° C. (or about 78° C.).

In some embodiments, the amount of free amines is related to the structural properties of the degradable bioprosthesis. In some embodiments, the amount of free amines on the degradable bioprosthesis has the ranges disclosed above. In some embodiments, the amount of free amines on the degradable bioprosthesis is proportional to the degradation rate of the degradable bioprosthesis. In some embodiments, the amount of free amines remaining on the degradable bioprosthesis is proportional to the shrinkage temperature, or denaturation temperature of the degradable bioprosthesis.

In some embodiments, the degradable bioprosthesis as described herein is formed into a flexible sheet of any shape and from 1 to 500 (or about 1 to about 500) square centimeters to be applied to the body. For example, a flexible sheet may be appropriately sized to be placed over treatment site. In some embodiments, the flexible sheet may be treated to include an antimicrobial agent to help prevent infection in the sheet or in the treatment site, and/or to deliver an antimicrobial agent into the treatment site to treat an existing infection. In some embodiments, the methods described above can be utilized to form a partially crosslinked skin substitute. The skin substitute may be a non-human tissue such as porcine tissue. The skin substitute may be processed such that the collagen-containing porcine tissue is only partially cross-linked, and for example, may be only 20%-80% (or about 20% to about 80%) crosslinked. In another embodiment, the collagen-containing tissue may be only 40%-60% (or about 40% to about 60%) crosslinked. The crosslinking of the tissue may be accomplished using the techniques described in U.S. Pat. No. 5,880,242, in combination with methods for achieving partial crosslinking as described above.

Method of Treating

Some embodiments provide a method for treating a tissue defect comprising positioning any of the degradable bioprostheses described herein at, over, or into the tissue defect. In some embodiments, the tissue defect is a wound. Some embodiments provide a method for treating a wound, for performing tissue repair, and/or for providing tissue and organ supplementation. In some embodiments, the first step of treating a tissue defect, wound, and/or supplementing and replacing tissue involves identifying a patient in need of a degradable bioprosthesis to aid in the remedying of a tissue defect, healing of a wound, or in need of a tissue supplement.

A non-limiting list of patients in need of a degradable bioprosthesis includes patients suffering tissue defects. In some embodiments, the patients in need of a degradable bioprosthesis suffer from wounds including those in need of skin substitutes for burns and skin ulcers. Degradable bioprostheses can also be used in the treatment of diabetic foot ulcers, venous leg ulcers, pressure ulcers, amputation sites, in other skin trauma, or in the treatment of other wounds or ailments. Patients in need of a degradable bioprosthesis also include patients in need of repair and supplementation of tendons, ligaments, fascia, and dura mater. Degradable prostheses can be used in supplement tissue in procedures including, but not limited to, rotator cuff repair, Achilles tendon repair, leg or arm tendon or ligament repair (e.g., torn ACL), vaginal prolapse repair, bladder slings for urinary incontinence, breast reconstruction following surgery, hernia repair, staple or suture line reinforcement, bariatric surgery repair, pelvic floor reconstruction, dural repair, gum repair, and bone grafting and reconstruction. Further, a patient in need of a degradable bioprosthesis also includes one in need of tissue or organ replacement. In some embodiments, the tailorably crosslinked collagen-based material described herein can be used to replace tissue or organs by acting as an artificial extracellular matrix. In such an application, this tailorably crosslinked collagen-based material can be used to support cell and tissue growth. Briefly, cells can be taken from a patient or a viable host and seeded on the tailorably crosslinked collagen-based material either in vivo or ex vivo. Then as the patient's natural tissues invade the crosslinked material, it is tailored to degrade and leave only naturally occurring tissues and cells. Other uses for the products and methods described herein may be for orthopedic surgery and for hernia repair, breast or other soft tissue reconstruction and urogynecological repair.

Skin substitutes or other materials or products made from the processing described above may be used in the treatment of topical and surgical chronic wounds, or in surgical reconstructive procedures. Whenever human or animal tissue (biologic products) is used in treating wounds, the body's normal immunological response is to recognize the foreign tissue and launch an enzymatic attack to degrade/dissolve the tissue collagen as rapidly as possible. Long ago it was shown that crosslinking the collagen molecules in biologic tissue could mask from the host body the foreign collagen and protect the foreign collagen from enzymatic attack.

In some embodiments, the treatment of an amputation site is performed using the degradable bioprosthesis. After amputation the surgically created stump commonly has problems healing due pressure and abrasion during healing process as well as adapting to artificial limbs. In some embodiments, the biodegradable bioprosthesis can be used to aid in the healing of these wounds and protecting them during the healing process.

The rotator cuff is a group of muscles and their tendons that act to stabilize the shoulder. In some embodiments, the degradable bioprosthesis can be used to augment, reinforce, or replace rotator cuffs with common tears or ruptures. Rotator cuff tears are common sports injuries and age related degenerative problems of the shoulder. In some embodiments, the degradable bioprosthesis can function as an adhesion barrier; adhesions are a common post-operative problem with repairs of this tendinous structure. In some embodiments, common tears or ruptures of the Achilles tendon can be augmented, reinforced or replaced with degradable bioprostheses. In some embodiments, the degradable bioprosthesis can also function as an adhesion barrier. Adhesions are a common problem with repairs of this tendon due to the long sliding action required as the foot goes through its normal range of motion. In some embodiments, the degradable bioprosthesis can be used to augment, reinforce, or replace tendons and ligaments from the leg, hand, arm, or any other body part.

In some embodiments, the degradable bioprosthesis provides additional necessary structural material and a biological material eliminating the need for permanent synthetic materials being left in the abdomen during vaginal prolapse treatment. Vaginal vault prolapse is a defect that occurs high in the vagina and entails a surgical approach through the vagina or abdomen. The surgical correction of this condition usually involves a technique called a vaginal vault suspension, in which the surgeon attaches the vagina to strong tissue in the pelvis or to a bone called the sacrum, which is located at the base of the spine. In some embodiments, the degradable bioprosthesis can be used to provide additional support for the suspension in the treatment of vaginal prolapse.

In some embodiments, the degradable bioprosthesis can be used as a bladder sling (or a pubovaginal fascial sling) in the treatment of urinary incontinence, During this type of operation the urologist attaches a piece of fascia (flat, tough, tendon-like material—about 1 inch wide and 5 inches long) around the bladder neck to keep urine in, even under stress. The slings are commonly made of human tissue from either the patient or a donor. In some embodiments, the degradable bioprosthesis can replace or augment the human donor material for this procedure. The sub urethral sling is commonly made of a synthetic mesh placed under the urethra which acts like a hammock, lifting and compressing the urethra, preventing leaks. In some embodiment, the degradable bioprosthesis can replace or augment this synthetic mesh.

In some embodiments, after mastectomy or traumatic injury to the breast, the degradable bioprosthesis can be used to repair or reconstruct missing structural collagen fibers, tendons and fascia during plastic surgery procedures.

In some embodiments, the degradable bioprosthesis can be used to reinforce or replace the surgical repair and reconstruction of the abdominal wall, fill gaps where insufficient tissue is remaining providing a scaffold for biologic remodeling, and promote in growth during hernia repair. Hernia results from the physical failure of the abdominal fascia and muscular structure allowing the protrusion of the contents of the body cavity. Adhesions are common in hernia. In some embodiments, the degradable bioprosthesis, can also act as an adhesion barrier post-operatively.

Suture lines, especially in more friable tissues such as lung tissue, weakened or degenerative tendenous materials, heart surgery, organ transplant to name a few require a pledget or suture reinforcement to prevent the suture or staple from "cheese wiring" or cutting through the thin or weakened tissue. In some embodiments, the degradable bioprosthesis can be used as a buttress to prevent cutting through of the suture or staple protecting the native tissue.

In some embodiments, the degradable bioprosthesis can be used in place or in conjunction with sutures or staples to provide a stable reconstruction of the stomach outer fascia and perimeter during bariatric surgery. Bariatric surgery to reduce the volume of the stomach is commonly done as a remedy for obesity.

In some embodiments, the degradable bioprosthesis can be used to reconstruct and support the weakened and damaged native connective tissue during pelvic floor reconstruction. Pelvic floor reconstructive surgery consists of several procedures for correcting a condition called pelvic organ prolapse. When the muscles of the pelvic floor are damaged or become weak—often due to childbirth—they are sometimes unable to support the weight of some or all of the pelvic and abdominal organs. If this occurs, one or more of the organs may drop (prolapse) below their normal positions, causing symptoms including discomfort, pain, pressure and urinary incontinence. The goal of pelvic floor reconstruction is to restore the normal structure and function of the female pelvic organs.

In some embodiments, after traumatic injury or brain surgery, the degradable bioprosthesis can be used to reseal or patch any perforations and leaks due to defect to the dura mater. Dura mater, the protective fascia covering of the brain is critical to maintain the fluid surrounding the brain.

In some embodiments, during the process of repairing damaged or disease bone segments, the degradable bioprosthesis can be surgically modeled to recreate missing segments or gaps in the repair or replacement of damaged bone throughout the skeletal structure. The collagen in cortical bone can retrieved from animal or human bone sourced material. The process of first demineralizing the bone and then cross-linking the remaining collagen structure can result in a material the can function as a semisolid bone void filler.

In some embodiments, the degradable bioprosthesis can provide an alternate source of material gum disease procedures. As a result of periodontal disease where gum tissue has been lost, the dentist or periodontist can surgically insert a soft tissue graft, in which synthetic material or tissue taken from another area of your mouth is used to cover exposed tooth roots. In some embodiments, the degradable bioprosthesis can be used to replace or supplement other materials used in the treatment of periodontal disease.

In some embodiments, after identifying a viable patient for the above methods of treating, the next step is to identify the rate at which the degradable bioprosthesis should degrade in order to work effectively. In some embodiments, this step involves determining the healing rate of the wound or other tissue defect. In some embodiments, this step involves determining the rate at which natural cell growth would reach a level at which the degradable bioprosthesis was no longer necessary.

Advantageously, skin substitute, wound, or other tissue defect treatment products made from the processes described above may be synchronized to degrade with the wound healing process. For example, a skin substitute made using the processes described herein may be tailored to begin to degrade at more or less a slow, but constant rate, that is synchronized with the healing process and the reduction in size of the wound, such that upon completion of wound healing, the crosslinked bioprosthetic product has been fully dissolved, with such process typically completed in 6-12 (or about 6 to about 12) weeks. In some embodiments, the degradation rate of the skin substitute is such that the skin substitute degrades completely within the range of time between about 8 weeks and about 1 year.

Other examples, such as surgical meshes, are made using the processes described herein and may be tailored to resist, or limit degradation, and thereby retain high tensile strength, for a period of time such as 1-3 (or about 1 to about 3) months or until such time as the surrounding, or new tissue has healed sufficiently to bear weight or absorb normal stresses without damage, after which the product continues to degrade at a slow, but constant, rate until it is fully dissolved, with such process typically completed in one year or about one year.

Depending on the rate of healing of the wound, a degradable bioprosthesis is then selected for use.

The final step involves implanting the degradable bioprosthesis. In some embodiments, this involves placing the degradable bioprosthesis at, over, or into the tissue defect. In some embodiments, the degradable bioprosthesis is surgically implanted into the patient at the target area. In some embodiments, the degradable bioprosthesis is surgically implanted into or over the wound. In some embodiments, the degradable bioprosthesis is affixed into or over the wound with stitches, glue, staples, or other adhesives. In some embodiments, the degradable bioprosthesis is first seeded with autologous or homologous cells before implantation.

In some embodiments, a partially crosslinked material or tailorably crosslinked collagen-based material, or any degradable bioprosthesis as described herein is formed into a flexible sheet of any shape and from 1 to 500 (or about 1 to about 500) square centimeters to be applied to the body. For example, a flexible sheet may be appropriately sized to be placed over treatment site. In some embodiments, the flexible sheet may be treated to include an antimicrobial agent to help prevent infection in the sheet or in the treatment site, and/or to deliver an antimicrobial agent into the treatment site to treat an existing infection.

In some embodiments, the product may be sterilized using various sterilization methods, including ethylene oxide, gamma, steam and e-beam. In some embodiments, a biologic skin substitute or other product may be sterilized in a manner that minimizes or prevents denaturing of collagen, such as by controlling the number of cycles, time, temperature and dose of radiation.

EXAMPLES

Materials and Equipment

The following is a list of materials and equipment used throughout the EXAMPLES section: Perkin Elmer Model DSC 4000, Differential Scanning calorimeter; Boekel Scientific Oven Model 132000; Mettler Toledo Analytic Balance Model AL54; Mettler Toledo Balance New Classic ML; Calipers, Mitutoyo Corp., 505-626 Dial Caliper; Labconco Lyophilizer Model Freezone 6 with Tray Dryer; Scalpel, Bard-parker Stainless Steel Sterile blade #10; Sklar Tru-Punch, Disposable Biopsy Punch; VWR SympHony SB70P pH Meter; Distilled Water; Sodium Dodecyl Sulfate Solution 0.1%; Sonic Bath=Bransonic 2510; Equine Pericardium; 0.9% NaCl Solution; 1,4 Butanediol Digylcidyl Ether; Standard HEPES Buffer; 0.1M Phosphate Buffer pH 4.5 (purchased from Teknova; Cat. #: P4000); Fixation Buffer pH 9.2.

Measuring Free Amine Content:

In addition to the tests described below, amine content can also be calculated. In some embodiments, the free amine group content of tailorably crosslinked collagen-based material, expressed as a percentage of the collagen-based material (%), can be determined using a 2,4,6-trinitrobenzenesulfonic acid (TNBS; 1.0 M solution in water, Fluka, Buchs, Switzerland) colorimetric assay. To a sample of 2-4 milligrams (mg) of tailorably crosslinked collagen-based material a solution of 1 ml of a 4% (weight/volume) aqueous $NaHCO_3$ (pH 9.0; Aldrich, Bornem, Belgium) solution and 1 ml of a freshly prepared 0.5% (weight/volume) aqueous TNBS solution can be added. After reaction for 2 hours at 40° C., 3.0 ml of 6 M HCl (Merck, Darmstadt, Germany) can be added and the temperature can be raised to 60° C. When complete solubilization of tailorably crosslinked collagen-based material is achieved, the resulting solution is diluted with 15 ml of deionized water and the absorbance was measured on a Hewlett-Packard HP8452A UV/VIS spectrophotometer at a wavelength of 345 nm. A control is prepared applying the same procedure except that HCl was added before the addition of TNBS. The free amine group content is calculated using a molar absorption coefficient of 14600 l mol$^{-1}$ cm$^{-1}$ for trinitrophenyl lysine [Wang C. L., et al., *Biochim. Biophys. Acta,* 544, 555-567, (1978)].

The free amine group content of tailorably crosslinked collagen-based material also can be determined using a ninhydrin test. The following describes the general procedures for testing the amine content of a collagen-based material. Briefly, a sample of 1-25 milligrams (mg) of tailorably crosslinked collagen-based material is collected. Next, a solution of 1 ml of a 4% (weight/volume) ninhydrin in methyl cello solve is prepared. Then a 0.2 M sodium citrate buffer is prepared by dissolving 1.05 g of citric acid monohydrate and 0.04 g of stannous chloride dihydrate in 11 mL of 1.0 N NaOH and adding 14 mL of purified water. The pH of the sodium citrate buffer is adjusted to 4.9 to 5.1 with HCl and/or NaOH. Next, the 4% ninhydrin solution and sodium citrate buffer are mixed in a dark bottle for immediate use. Now a solution of N-acetyllysine (ALys) is prepared by dissolving 47.1 mg of ALys in 50 mL of purified water. The ALys is used as a standard solution for calibrating the absorbance which is read at 570 nm. After a standard curve is plotted, samples of dried tissue are tested. Each solution for to be read by absorbance is prepared using 1 mL of buffered ninhydrin, 100 microliters of purified water, and the tissue or control sample. The test solutions are heated to 100° C. for 20 minutes, cooled, then 5 mL of isopropyl alcohol is added. The absorbance is then read and the amount of mols of amine per gram of sample and control is calculated from using the following equation: $A=mX+b$ where, A=absorbance, X=content of ALys in micromoles, m=the slope, and b=the y-intercept. The content of micromoles of free amine in the sample is then $X_{samp}=(A_{samp}-b)/m$.

Mechanical Properties:

Stress-strain curves of the degradable bioprosthesis can be taken using uniaxial measurements using a mechanical tester. Tensile bars (40.0 mm×4.0 mm×1.4 mm) can be cut using a dumb-bell shaped knife and can be hydrated for at least one hour in PBS at room temperature. The thickness of the samples can be measured in triplicate using a spring-loaded type micrometer (Mitutoyo, Tokyo, Japan). An initial gauge length of 10 mm was used and a crosshead speed of 5 mm/minute can be applied until rupture of the test specimen occurs. A preload of 0.05 N can be applied to prestretch the specimen before the real measurement. The tensile strength, the elongation at alignment, the elongation at break, the low strain modulus and the high strain modulus of the sample can be calculated from five independent measurements.

Preparation of Pericardium to Form Collagen-Based Material:

Equine pericardial sacks were procured fresh from Carnicos de Jerez S.A. de C.V. and air freighted in 0.9% NaCl solution on ice. Immediately on receipt, all sacks were rinsed in fresh, cold 0.9% NaCl solution, debrided of fat and excess fibrous tissue, and trimmed with a surgical scalpel to create 8 similar patches approximately 10 cm×15 cm. All patches were decellularized by a process of 20 minutes sonication in a 0.1% solution of Sodium Dodecyl Sulfate (SDS) followed by three separate rinses in 500 ml of 0.9% NaCl solution to remove excess SDS. The decellularization process is intended to remove any excess intracellular materials. The anionic surfactant (SDS) used in the process also helps to reduce excess fats and oils. The treatment of the resulting patches yielded 8 debrided, decellularized pericardial patches. One of these patches was set aside as a control for crosslinking experiments.

Preparation of Crosslinking Solutions:

To 1 L of deionized water was added potassium carbonate (6.5 grams) and sodium bicarbonate (16.6 grams). The solution was mixed until all solids dissolved. The pH of the solution was measured using a pH meter wherein the target pH was 9.2±0.2. If necessary, the pH of the solution was adjusted to 9.2±0.2 by adding dilute NaOH or dilute HCl. Next, to the buffered solution (bicarbonate buffer) was added BDDGE (40 g) to afford a 4% by weight solution of BDDGE. This solution was stirred to give a homogenous solution of 9.2±0.2 pH BDDGE.

To a solution phosphate buffered solution (PBS, 0.5 L, 4.5±0.2 pH) was added BDDGE (20 g) to afford a 4% by weight solution of BDDGE. This solution was stirred to yield a homogeneous solution of 4.5±0.2 pH BDDGE.

Example 1

To a low pH solution of BDDGE (4.0% w/v BDDGE, 4.5±0.2 pH, excess) was added, an approximately 10×15 cm debrided, decellularized pericardial patch. The patch was allowed to remain in the BDDGE/PBS solution for 160 hours at which time the patch was rinsed with distilled water thoroughly.

Example 2

To a high pH solution of BDDGE (4.0% w/v BDDGE, 9.2±0.2 pH, excess) was added, an approximately 10×15 cm debrided, decellularized pericardial patch. The patch was allowed to remain in the 4.0% w/v BDDGE, 9.2±0.2 pH solution for 8 hours, at which time it was added to a low pH solution of BDDGE (4.0% w/v BDDGE, 4.5±0.2 pH, excess). After 152 hours, the patch was removed from the low pH BDDGE solution and was rinsed with distilled water thoroughly.

Example 3

To a high pH solution of BDDGE (4.0% w/v BDDGE, 9.2±0.2 pH, excess) was added, an approximately 10×15 cm debrided, decellularized pericardial patch. The patch was allowed to remain in the 4.0% w/v BDDGE, 9.2±0.2 pH solution for 24 hours, at which time it was added to a low pH solution of BDDGE (4.0% w/v BDDGE, 4.5±0.2 pH, excess). After 136 hours, the patch was removed from the low pH BDDGE solution and was rinsed with distilled water thoroughly.

Example 4

To a high pH solution of BDDGE (4.0% w/v BDDGE, 9.2±0.2 pH, excess) was added, an approximately 10×15 cm debrided, decellularized pericardial patch. The patch was allowed to remain in the 4.0% w/v BDDGE, 9.2±0.2 pH solution for 36 hours, at which time it was added to a low pH solution of BDDGE (4.0% w/v BDDGE, 4.5±0.2 pH, excess). After 124 hours, the patch was removed from the low pH BDDGE solution and was rinsed with distilled water thoroughly.

Example 5

To a high pH solution of BDDGE (4.0% w/v BDDGE, 9.2±0.2 pH, excess) was added, an approximately 10×15 cm debrided, decellularized pericardial patch. The patch was allowed to remain in the 4.0% w/v BDDGE, 9.2±0.2 pH solution for 48 hours, at which time it was added to a low pH solution of BDDGE (4.0% w/v BDDGE, 4.5±0.2 pH, excess). After 112 hours, the patch was removed from the low pH BDDGE solution and was rinsed with distilled water thoroughly.

Example 6

To a high pH solution of BDDGE (4.0% w/v BDDGE, 9.2±0.2 pH, excess) was added, an approximately 10×15 cm debrided, decellularized pericardial patch. The patch was allowed to remain in the 4.0% w/v BDDGE, 9.2±0.2 pH solution for 64 hours, at which time it was added to a low pH solution of BDDGE (4.0% w/v BDDGE, 4.5±0.2 pH, excess). After 96 hours, the patch was removed from the low pH BDDGE solution and was rinsed with distilled water thoroughly.

Example 7

Figure 2:
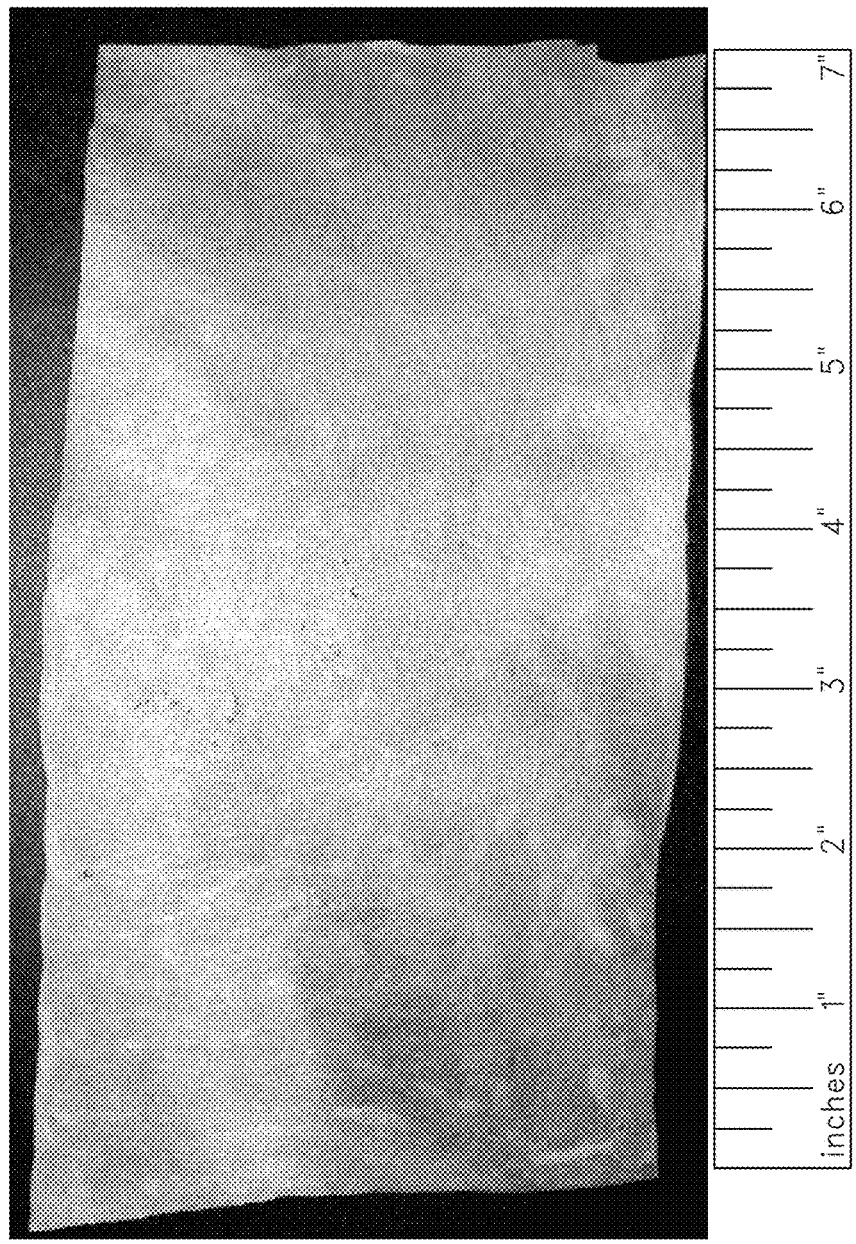
FIG. 2 depicts one embodiment of crosslinked collagen-based material made using the process described herein.

To a high pH solution of BDDGE (4.0% w/v BDDGE, 9.2±0.2 pH, excess) was added, an approximately 10×15 cm debrided, decellularized pericardial patch. The patch was allowed to remain in the 4.0% w/v BDDGE, 9.2±0.2 pH solution for 160 hours, at which time the patch was removed from the low pH BDDGE solution and was rinsed with was rinsed with distilled water thoroughly. FIG. 2 depicts a sheet of collagen-based material crosslinked for 160 hours at pH 9.2 with BDDGE. Each of the collagen materials from Examples 1-6 are identical in appearance to the FIG. 2 material when viewed with the naked eye.

Temperature of Shrinkage (Ts):

Three 3 mm diameter samples were cut from each of the resulting crosslinked materials from examples 1-7 and the control using a Skylar 3 mm biopsy punch.

Each sample was sealed in a Perkin Elmer DSC volatile sample pan (0219-0062). An empty pan is run in parallel with the test sample in the Differential Scanning calorimeter (DSC). Through comparison of heat flow of the empty pan and test pan, the peak temperature of enthalpy indicates the transition temperature or temperature of shrinkage (Ts) of the sample expressed in ° C.

Figure 3:
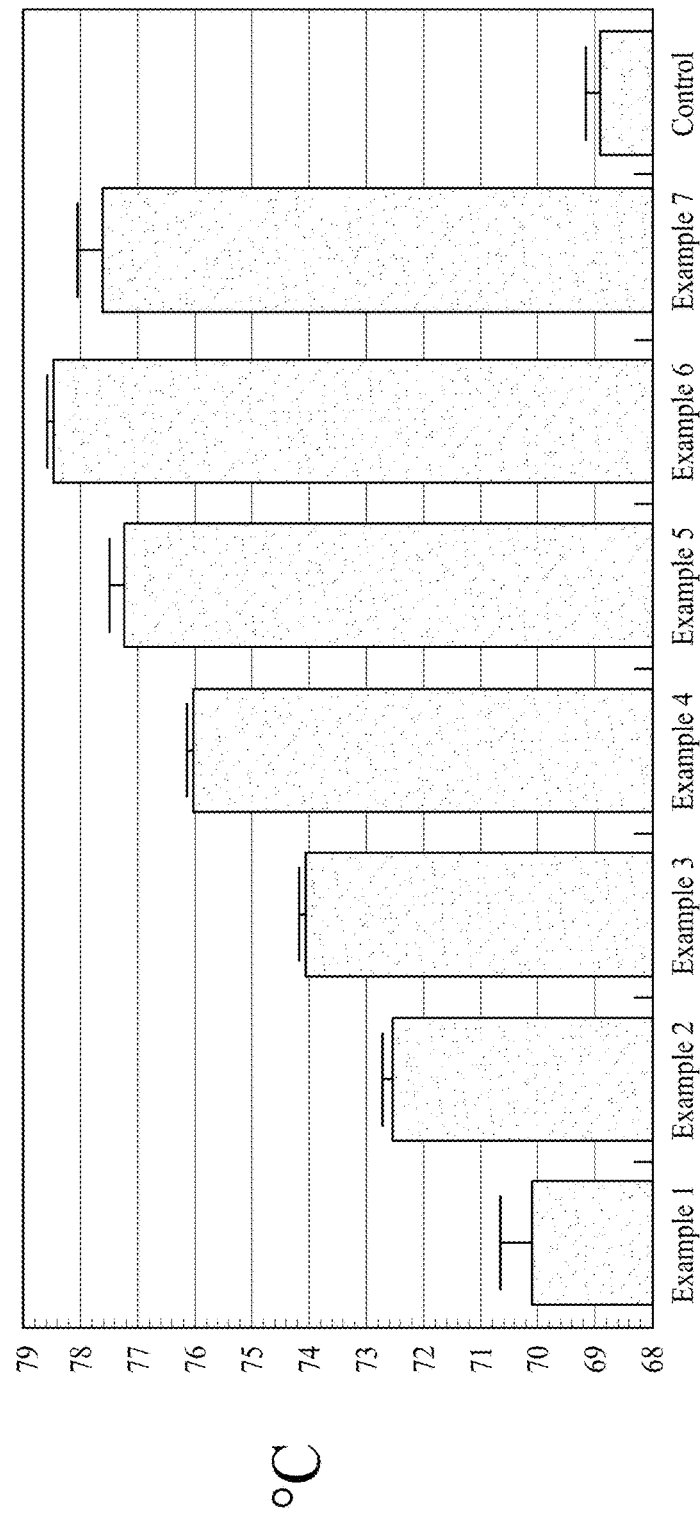
FIG. 3 is a chart showing the temperature of shrinkage for Examples 1-7 and native collagen.

Ts of the samples are compared to that of the control or non-cross-linked to determine the comparative level of amine cross-linking present. Table 1 contains the results of each sample, separated by each example number. FIG. 3 contains a graphical depiction of the results from Table 1.

TABLE 1

Temperature of Shrinkage Results (° C.)

| | Sample # | | | | |
|---|---|---|---|---|---|
| | 1 | 2 | 3 | Ave | SD |
| Example 1 | 69.63 | 70.90 | 69.71 | 70.08 | 0.58 |
| Example 2 | 72.81 | 72.40 | 72.41 | 72.54 | 0.19 |
| Example 3 | 73.91 | 74.09 | 74.19 | 74.06 | 0.12 |
| Example 4 | 76.17 | 75.98 | 76.03 | 76.06 | 0.08 |
| Example 5 | 78.31 | 78.54 | 78.53 | 78.46 | 0.11 |
| Example 6 | 77.58 | 77.11 | 76.98 | 77.22 | 0.26 |
| Example 7 | 77.26 | 77.30 | 78.21 | 77.59 | 0.44 |
| Control | 69.19 | 68.94 | 68.55 | 68.89 | 0.26 |

Pronase Digestion Assay

Three 1 cm×1 cm samples were cut from each of examples 1-7 and the control and tested per MF3-00X Pronase Digestion. Per procedure MF3-00X each sample was placed in a 5 ml glass scintillation vial with 4 mls of a HEPES buffered solution with 95 mg/100 ml bacterial protease derived from *Streptomyces griseus*.

The samples were incubated at 45° C. for 24 hours, blotted dry and lyophilized in the Labconco lyophilizer. Then each sample was weighed utilizing the Mettler Toledo analytic balance. All samples were reweighed using the Mettler Toledo analytic balance.

Figure 4:
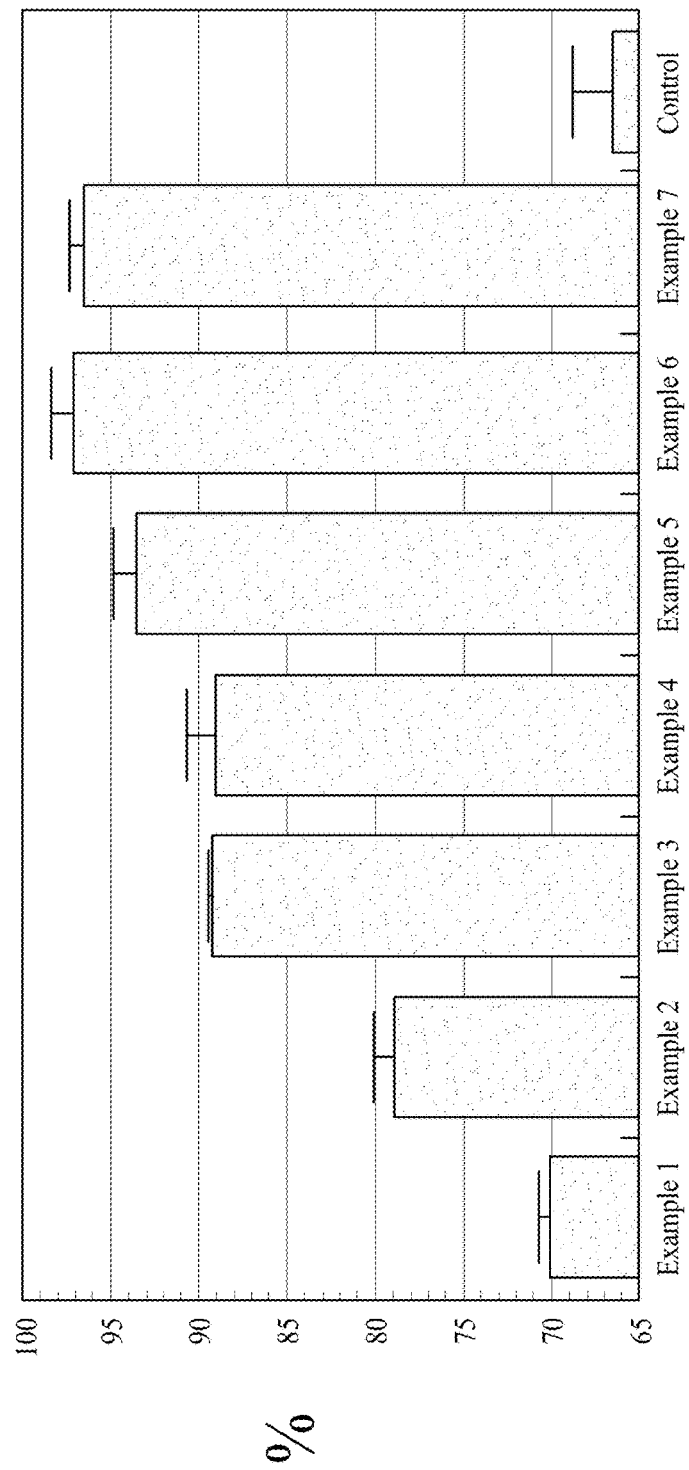
FIG. 4 is a chart showing the resistance of protease digestion of Examples 1-7 and native collagen.

The percent degradation was determined calculating the percent change in weight before and after 24 hours exposure to the protease. Table 2 contains the results of each sample, separated by each example number. FIG. 4 contains a graphical depiction of the results from Table 2.

TABLE 2

Protease Digestion % After 24 Hours Exposure to Protease

| | Sample # Wt. (mg) after/before | | | Ave % | |
|---|---|---|---|---|---|
| | 1 | 2 | 3 | Remaining | SD |
| Example 1 | 5.30/7.60 | 5.40/7.30 | 5.60/7.30 | 73.47% | 2.87 |
| Example 2 | 7.80/10.10 | 8.30/10.50 | 10.60/13.20 | 78.86% | 1.26 |
| Example 3 | 10.60/11.90 | 10.80/12.20 | 12.40/13.80 | 89.15% | 0.55 |
| Example 4 | 10.50/11.90 | 11.30/12.90 | 12.70/13.90 | 89.07% | 1.65 |
| Example 5 | 14.30/14.80 | 15.70/16.00 | 19.80/20.50 | 97.11% | 0.72 |
| Example 6 | 5.00/5.40 | 6.10/6.40 | 5.10/5.50 | 93.54% | 1.25 |
| Example 7 | 11.50/12.00 | 12.10/12.60 | 12.60/12.90 | 96.51% | 0.83 |
| Control | 8.60/13.40 | 8.80/13.40 | 9.40/13.50 | 66.49% | 2.30 |

Figure 5:
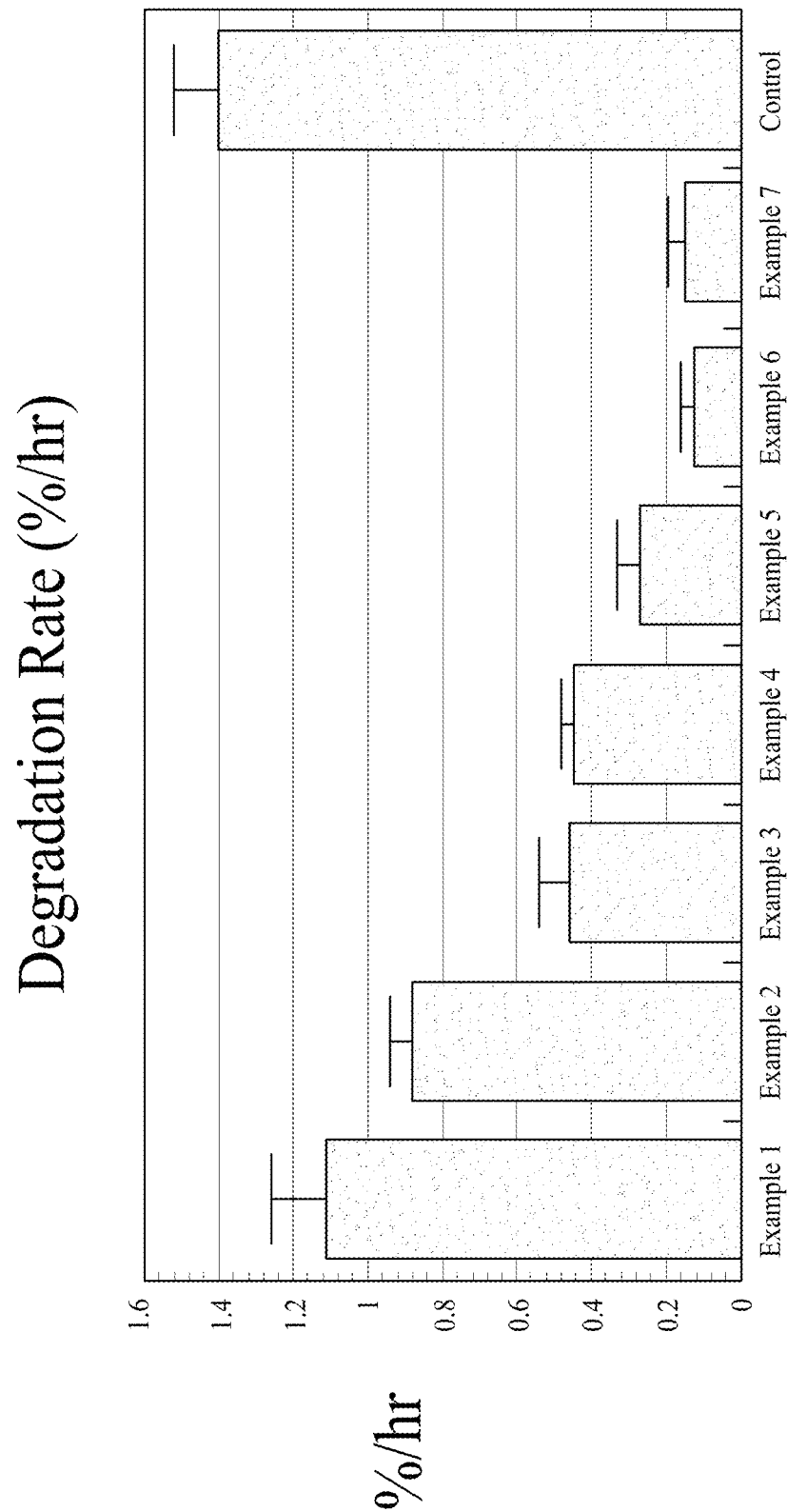
FIG. 5 is a chart showing the degradation rates (in % mass loss per hour) of Examples 1-7 and native collagen.

The degradation rate was then calculated by dividing the % digestion after 24 hours by 24 hours to yield % degraded/hour. Table 3 shows those results. FIG. 5 contains a graphical depiction of the results from Table 3.

TABLE 3

Degradation Rate in %/hr.

| | Sample # | | | | |
|---|---|---|---|---|---|
| | 1 | 2 | 3 | Ave | SD |
| Example 1 | 1.26 | 1.08 | 0.97 | 1.11 | 0.15 |
| Example 2 | 0.95 | 0.87 | 0.82 | 0.88 | 0.06 |
| Example 3 | 0.46 | 0.48 | 0.42 | 0.45 | 0.03 |
| Example 4 | 0.49 | 0.52 | 0.36 | 0.46 | 0.08 |
| Example 5 | 0.14 | 0.08 | 0.14 | 0.12 | 0.04 |
| Example 6 | 0.31 | 0.20 | 0.30 | 0.27 | 0.06 |
| Example 7 | 0.17 | 0.17 | 0.10 | 0.15 | 0.04 |
| Control | 1.49 | 1.43 | 1.27 | 1.40 | 0.12 |

The study demonstrated that a pH shift from high (9.2) to low (4.5) within the first 64 hours of a 160 hour 4% BDDGE cross-linking process resulted in an extracellular collagen matrix with progressively lower Ts values, lower resistance to protease and a significantly faster bioresorbtion rate.

The process of pH modulation of the BDDGE cross-linking process of extracellular collagen matrix material is a feasible method of producing a medical device for general surgical repair with a controlled predetermined bioresorbtion rate.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein. Certain embodiments of the invention are encompassed in the claim set listed below.

What is claimed is:

1. A method of treating a tissue defect comprising:
positioning a degradable bioprosthesis at, over, or into the tissue defect, wherein the degradable bioprosthesis comprises:
a crosslinked collagen-based material comprising Crosslink A, Crosslink B, and free amines (—$NH_2$):

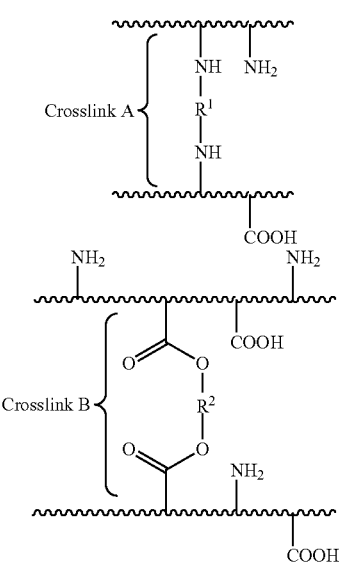

wherein:
~~~ indicates collagen strands;
$R^1$ is

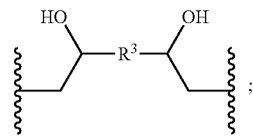

$R^2$ is

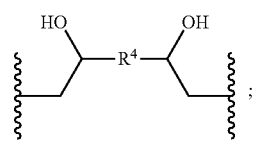

$R^3$ and $R^4$ are independently selected from the group consisting of —$CH_2$—O—($CH_2$)$_n$—O—$CH_2$— and —$CH_2$—(O($CH_2$)$_n$)$_m$—O—$CH_2$—, and
n and m are independently an integer from 1-6;
wherein the crosslinked collagen based material has a degradation rate between about 0.2% to about 1.0% per hour during the first 24 hours of exposure to a pronase digestion assay.

2. The method of claim 1, wherein the tissue defect is a defect selected from the group consisting of a tendon defect, a ligament defect, vaginal prolapse, a hernia, a tissue defect that causes urinary incontinence, a gum defect, an organ defect, a tissue defect that results from bariatric surgery, and a wound.

3. The method of claim 1, wherein the tissue defect is a tendon defect.

4. The method of claim 1, wherein the tissue defect is a ligament defect.

5. The method of claim 1, wherein the tissue defect is vaginal prolapse.

6. The method of claim 1, wherein the tissue defect is a hernia.

7. The method of claim 1, wherein the tissue defect causes urinary incontinence.

8. The method of claim 1, wherein the tissue defect is a gum defect.

9. The method of claim 1, wherein the tissue defect is an organ defect.

10. The method of claim 1, wherein the tissue defect is as a result of bariatric surgery.

11. The method of claim 1, wherein the tissue defect is a wound.

12. The method of claim 1, wherein the degradable bioprosthesis is derived from animal pericardium.

13. The method of claim 1, wherein the degradable bioprosthesis is attached to the tissue defect.

14. The method of claim 1, wherein the degradable bioprosthesis comprises a flexible sheet.

15. The method of claim 14, wherein the flexible sheet is between about 1 cm$^2$ and about 500 cm$^2$.

16. The method of claim 14, wherein the flexible sheet is treated with antimicrobial agent.

\* \* \* \* \*